US006887904B2

(12) United States Patent
Mailliet et al.

(10) Patent No.: US 6,887,904 B2
(45) Date of Patent: May 3, 2005

(54) SUBSTITUTED ARYLCYCLOALKANES, COMPOSITIONS CONTAINING THEM AND USE THEREOF

(75) Inventors: Patrick Mailliet, Fontenay sous Bois (FR); Marc Capet, Melesse (FR); Gilles Tiraboschi, Montgeron (FR); Thomas Caulfield, Paris (FR)

(73) Assignee: Aventis Pharma S. A., Antony Cedex (FR)

( * ) Notice: Subject to any disclaimer, the term of this patent is extended or adjusted under 35 U.S.C. 154(b) by 127 days.

(21) Appl. No.: 10/309,250

(22) Filed: Dec. 4, 2002

(65) Prior Publication Data

US 2003/0149072 A1 Aug. 7, 2003

Related U.S. Application Data

(60) Provisional application No. 60/346,901, filed on Jan. 11, 2002.

(30) Foreign Application Priority Data

Dec. 5, 2001 (FR) .............................. 01 15740

(51) Int. Cl.$^7$ ....................... C07C 49/84; A61K 31/122
(52) U.S. Cl. ..................... 514/646; 514/679; 514/681; 514/683; 514/684; 564/443; 568/326; 568/327; 568/329; 568/330
(58) Field of Search ................ 568/326, 327, 568/329, 330; 564/443; 514/679, 681, 683, 684, 646

(56) References Cited

U.S. PATENT DOCUMENTS 4,904,697 A    2/1990  Sunkara et al.

FOREIGN PATENT DOCUMENTS

EP          0 288 794        11/1988

OTHER PUBLICATIONS

Prinz, PubMed Abstract (Expert Rev Anticancer Ther. 2(6):695–708) Dec. 2002.*
Dabydeen et al., A quantitative evaluation of the effects of inhibitors of tubulin assembly on polymerization induced by discodermolide epothilone B, and paclitaxel, Cancer Chemother Pharmacol 53: 397–403, 2004.*

Simone, Oncology: Introduction, Cecil Textbook of Medicine, 20$^{th}$ Edition, vol. 1, pp. 1004–1010, 1996.*

Murphy et al., "Lewis Acid–Catalysed Reactions Of Aryl Cyclopropyl Ketones. Scope and Mechanism," *Journal of the Chemical Society, Perkin Transactions 1*, 4:1029–1035 (1982).

Murphy et al., "Reactions Of Aryl Cyclopropyl Ketones. A New Synthesis Of Aryl Tetralones," *Journal of the Chemical Society, Perkin Transactions 1*, 4:2920–2926 (1981).

Lokanatha Rai et al., "An Improved Method For The Synthesis Of Cyclopropyl Ketoesters," *Synthetic Communications*, 20(9): 1273–1277 (1990).

Lygo et al., "Asymmetric Phase–Transfer Mediated Expoxidation Of Alpha,Beta–Unsaturated Ketones Using Catalysts Derived From *Cinchona* Alkaloids," *Tetrahedron Letters*, 39(12): 1599–1602 (1998).

Murphy et al., "Trapping The Intermediate Invovled In The Intramolecular Cyclisation Of Cyclopropyl Ketones. A Convenient Preparation Of Open–Chain Gamma–Hydroxy Ketones," *Tetrahedron Letters*, 21(36): 3517–3520 (1980).

Murphy et al., "An Improved Route To An Intermediate in Podophyllotoxin Synthesis," *Journal of the Chemical Society, Chemical Communications*, 6:262–263 (1980).

Edwards et al., "Chalcones: A New Class Of Antimitotic Agents," *Journal of Medicinal Chemistry*, 33(7): 1948–1954 (1990).

* cited by examiner

*Primary Examiner*—Deepak Rao
(74) *Attorney, Agent, or Firm*—Balaram Gupta

(57) ABSTRACT

Substituted arylcycloalkanes, compositions containing them and use thereof. The present invention relates especially to substituted arylcycloalkanes with therapeutic activity, which may be used such as in oncology.

13 Claims, No Drawings

SUBSTITUTED ARYLCYCLOALKANES, COMPOSITIONS CONTAINING THEM AND USE THEREOF

The present application claims priority under 35 U.S.C. § 119(e) of U.S. Provisional Application No. 60/346,901, filed Jan. 11, 2002, the disclosure of which is expressly incorporated by reference herein. The present application also claims priority under 35 U.S.C. § 119 of French Application No. 0115740, filed Dec. 5, 2001, the disclosure of which is expressly incorporated by reference herein.

The present invention relates to chemical compounds, such as arylcycloalkanes, to compositions containing them and to their use as medicinal products.

The invention also relates to novel arylcycloalkanes with anticancer activity, such as inhibitory activity on tubulin polymerization.

The arylcycloalkanes which are of concern herein are carbocyclic derivatives of chalcones, in which the prop-2-en-1-one chain is replaced with a propanone chain in which positions 2 and 3 are substituted with an alkyl or alkenyl chain linked simultaneously to positions 2 and 3 of the propanone chain.

Michael L. Edwards et al., in the article published in *J. Med. Chem.* 1990, vol. 33, pp. 1948–1954, present chalcones that may be used as antimitotic agents.

Compound 81, presented in Table IV, is a reduced linear chalcone. Its modest anticancer activity relative to its unsaturated analog 36, presented in Table III, naturally led the authors away from reduced products.

In addition, although the substitution of a hydrogen in position 2 on the prop-2-en-1-one chain entails a substantial improvement in activity (compound 63, Table III), the substitution of a hydrogen in position 3 on the same chain destroys the antitumor activity (compound 90, Table IV).

Unsaturated chalcones are therefore good candidates for the preparation of anticancer compositions. Unfortunately, it has been observed that unsaturated chalcones show major deficiencies in terms of stability. Thus, a prolonged exposure to light and/or air brings about a rapid degradation of the products, which is relatively incompatible with a use of medicinal products after prolonged storage for a period which may frequently range from a few months to one or more years.

Thus, it has been found that there is a need for chalcone derivatives which simultaneously exhibit increased stability and satisfactory activity, such as with respect to the inhibition of tubulin polymerization.

These requirements are addressed by the products of the present invention, which correspond to formula (I) below:

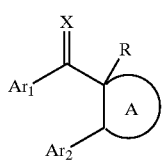

(I)

in which:
A represents a saturated or partially unsaturated, optionally substituted cyclic hydrocarbon containing from 3 to 14 carbon atoms;
X is selected from the group consisting of O and N—O—(R2),
each radical R or (R2) is independently selected from the group consisting of H, C1–C7 alkyl, cyclo(C3–C9) alkyl(C1–C7)alkyl, aryl(C1–C7)alkyl-, substituted C1–C7 alkyl, substituted cyclo(C3–C9)alkyl(C1–C7) alkyl- and substituted aryl(C1–C7)alkyl-, or R is a halogen and (R2) is as defined above, $Ar_1$ represents a first phenyl nucleus, substituted with 1 to 4 radicals O(R3), in which R3 is independently selected from the group consisting of H and C1–C3 alkyl, and in which an R3 may be simultaneously linked to two adjacent oxygen atoms borne by the first phenyl nucleus, $Ar_2$ represents:
a second phenyl nucleus substituted with one or more radicals R4, in which each of the radicals R4 is independently selected from the group consisting of hydrogen, halogen, hydroxyl, C1–C4 alkyl, C1–C3 alkoxy, C1–C3 alkylthio, amino, C1–C3 alkylamino and C1–C3 dialkylamino, it being understood that each of the radicals R4, with the exception of R4=hydrogen and R4=halogen, may be substituted with a functional group G1 allowing the solubility of the product of formula (I) to be increased, in which said functional group G1 either (i) does not significantly affect the biological activity of the product of formula (I), or (ii) is a prodrug;
a 5- to 12-membered nitrogenous aromatic heterocycle, optionally substituted with one or more radicals R4.

One of the merits of the invention is that of having discovered that it is possible to obtain saturated chalcone derivatives (containing a 1,3-diarylpropanone unit) with satisfactory activity against tubulin polymerization.

One of the other merits of the invention is that of having discovered that it is possible, surprisingly, to substitute position 3 of the prop-2-en-1-one chain with a hydrocarbon-based radical while at the same time maintaining satisfactory activity against tubulin polymerization, when said hydrocarbon-based radical is linked to position 2 of the prop-2-en-1-one, and that said propenone is reduced to a propanone.

One of the other merits of the invention is that of having discovered that, against all expectation, the addition of a substituent linked simultaneously to positions 2 and 3 of a 1,3-diarylpropanone reputed to be inactive or only slightly active against tubulin polymerization, leads to the production of compounds that inhibit tubulin polymerization.

A may be chosen from monocyclic and bicyclic hydrocarbons containing from 3 to 8 carbon atoms.

A may also be a cyclopropyl.

X may be oxygen.

R may be selected from the group consisting of H, halogen, $CH_3$, $CF_3$, $C_2H_5$ and $C_3$–$C_4$ alkyl.

The first phenyl nucleus $Ar_1$ may be substituted with a substituent or a group of substituents chosen from:
(i) 1 to 4 $OCH_3$ radicals,
(ii) a methylenedioxy radical,
(iii) an ethylenedioxy radical,
(iv) 1 or 2 $OCH_3$ radicals and a methylenedioxy radical,
(v) 1 or 2 $OCH_3$ radicals and an ethylenedioxy radical.

$Ar_1$ may be substituted with a group of substituents chosen from:
(i) 2,5-dimethoxy,
(ii) 3,5-dimethoxy,
(iii) 2,3,4-trimethoxy,
(iv) 3,4,5-trimethoxy,
(v) 2,4,5-trimethoxy,
(vi) 2,3,5-trimethoxy,
(vii) 2,3,4,5-tetramethoxy, (viii) 3,4-methylenedioxy,
(ix) 3,4-ethylenedioxy Ar$_1$ may also be chosen from 2,5-dimethoxyphenyl and 3,4,5-trimethoxyphenyl.

Ar$_2$ may be a phenyl nucleus substituted with one or more groups R4 selected from the group consisting of hydroxyl, methoxy, ethoxy, amino, C1–C3 alkylamino, C1–C3 dialkylamino, OPO$_3$M$_2$, OSO$_3$M, NH-amino acid and N(alkyl)-amino acid; in which:
1) M is selected from the group consisting of (i) H, (ii) an alkali metal, (iii) a combination of alkali metals, (iv) a combination of H and of an alkali metal, for example OPO$_3$HNa;
2) the amino acid is linked to NH or N(alkyl) to form a cleavable amide bond, for example by a peptidase.

Ar$_2$ may be selected from the group consisting of 3-hydroxy-4-methoxyphenyl; 4-hydroxy-3-methoxyphenyl; 3-hydroxy-4-aminophenyl; 4-hydroxy-3-aminophenyl; 3-hydroxy-4-(N,N-dimethylamino)phenyl; 4-hydroxy-3-(N,N-dimethylamino)phenyl.

A product in accordance with the invention may be:
1) in racemic form, or
2) in a form enriched in a stereoisomer; or
3) in a form enriched in an enantiomer; and may optionally be salified.

A product in accordance with the invention may have the formula (I) below:

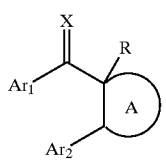

(I)

in which:

A represents a saturated or partially unsaturated monocycloalkyl or bicycloalkyl radical containing from 3 to 14 carbon atoms, optionally substituted with one or more groups chosen from halogen atoms and C1–C7 alkyl, amino, C1–C7 alkylamino, C1–C7 dialkylamino, hydroxyl, C1–C7 alkoxy, C1–C7 alkylthio, carbonyl, cyano, trifluoromethyl, carboxyl, (C1–C7) alkoxycarbonyl, carboxamido, N—[(C1–C7)alkyl] carboxamido or N,N—[(C1–C7)dialkyl]carboxamido radicals, optionally a fused C6–C10 aryl group, for example phenyl or naphthyl, or with a fused C2–C13 heteroaryl group, for example 1,2,3-triazolo[c]-, pyrido-, carbazolo- or acridino-;

X represents an oxygen atom, a radical N—OR' in which R' represents a C1–C7 alkyl or aryl(C1–C7)alkyl-radical optionally substituted with an amino radical, C1–C7 alkylamino, C1–C7 dialkylamino, hydroxyl, C1–C7 alkoxy, C1–C7 alkylthio, carboxyl, (C1–C7) alkoxycarbonyl, carboxamido, N—[(C1–C7)alkyl] carboxamido or N,N—[(C1–C7)dialkyl]carboxamido;

R represents a hydrogen or halogen atom, a C1–C7 alkyl or aryl(C1–C7)alkyl-radical optionally substituted with one or more amino, alkylamino, dialkylamino, hydroxyl, alkoxy, alkylthio, carboxyl, alkoxycarbonyl, carboxamido, N-alkylcarboxamido or N,N-dialkylcarboxamido radicals;

Ar$_1$ represents a first phenyl nucleus substituted with 1 to 4 methoxy radicals, or a methylenedioxy radical, or an ethylenedioxy radical, or 1 or 2 methoxy radicals and a methylenedioxy radical, or 1 or 2 methoxy radicals and an ethylenedioxy radical;

Ar$_2$ represents:
a second phenyl nucleus substituted with one or more groups chosen from halogen atoms and hydroxyl, C1–C4 alkyl, C1–C3 alkoxy, C1–C3 alkylthio, amino, C1–C3 alkylamino and C1–C3 dialkylamino radicals, it being understood that the hydroxyl or amino radicals may be in the form of a cleavable, more water-soluble prodrug such as, in a nonlimiting manner, a phosphate or an amino acid derivative, or
a 5- to 12-membered nitrogenous heterocycle containing 1 or 2 nitrogen atoms, e.g., chosen from 3-pyridyl, 4-pyridyl, 4-pyrimidinyl, 6-quinolyl, 7-quinolyl, 6-isoquinolyl, 7-isoquinolyl, 6-quinazolinyl, 6-quinoxalinyl, N-alkyl-5-indolyl, N-alkyl-6-indolyl, N-alkyl-1,2,3,4-tetrahydro-6-quinolyl, N-alkyl-1,2,3,4-tetrahydro-7-quinolyl, 2-acridinyl, 3-acridinyl, N-alkyl-2-carbazolyl and N-alkyl-3-carbazolyl,
it being understood that the relative stereochemistry of the groups C(O)Ar$_1$ and Ar$_2$ on the cycloalkyl A may be trans.

A product in accordance with the invention corresponding to formula (I) described above may comprise a group A representing a saturated or partially unsaturated monocycloalkyl or bicycloalkyl radical containing from 3 to 8 carbon atoms.

The list of products below is also representative of the invention:

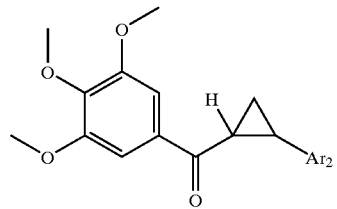

[2-(3-hydroxy-4-methoxyphenyl)cyclopropyl](3,4,5-trimethoxyphenyl)methanone,
[2-(3-amino-4-methoxyphenyl)cyclopropyl](3,4,5-trimethoxyphenyl)methanone
[2-(4-dimethylaminophenyl)cyclopropyl](3,4,5-trimethoxyphenyl)methanone
[2-(4-methoxyphenyl)cyclopropyl](3,4,5-trimethoxyphenyl)methanone
[2-(4-ethoxyphenyl)cyclopropyl](3,4,5-trimethoxyphenyl)methanone
[2-(3-hydroxy-4-methylphenyl)cyclopropyl](3,4,5-trimethoxyphenyl)methanone
[2-(3-amino-4-methylphenyl)cyclopropyl](3,4,5-trimethoxyphenyl)methanone
[2-(3-hydroxy-4-fluorophenyl)cyclopropyl](3,4,5-trimethoxyphenyl)methanone
[2-(3-amino-4-fluorophenyl)cyclopropyl](3,4,5-trimethoxyphenyl)methanone
[2-(3-hydroxy-4-dimethylaminophenyl)cyclopropyl](3,4,5-trimethoxyphenyl)methanone
[2-(3-amino-4-dimethylaminophenyl)cyclopropyl](3,4,5-trimethoxyphenyl)methanone
{2-[1-methyl(ethyl)indol-5-yl]cyclopropyl}(3,4,5-trimethoxyphenyl)methanone
{2-[1-methyl(ethyl)-1,2,3,4-tetrahydroquinol-6-yl]cyclopropyl}(3,4,5-trimethoxyphenyl)methanone
{2-[1-methyl(ethyl)carbazol-4-yl]cyclopropyl}(3,4,5-trimethoxyphenyl)methanone
2-methoxy-5-[1-(3,4,5-trimethoxyphenylcarbonyl]cycloprop-2-yl}phenoxyphosphoric acid 2-methyl-5-[1-(3,4,5-trimethoxyphenylcarbonyl]cycloprop-2-yl}phenoxyphosphoric acid
2-fluoro-5-[1-(3,4,5-trimethoxyphenylcarbonyl]cycloprop-2-yl}phenoxyphosphoric acid
2-dimethylamino-5-[1-(3,4,5-trimethoxyphenylcarbonyl]cycloprop-2-yl}phenoxyphosphoric acid
sodium 2-methoxy-5-[1-(3,4,5-trimethoxyphenylcarbonyl]cycloprop-2-yl}phenoxyphosphate
sodium 2-methyl-5-[1-(3,4,5-trimethoxyphenylcarbonyl]cycloprop-2-yl}phenoxyphosphate
sodium 2-fluoro-5-[1-(3,4,5-trimethoxyphenylcarbonyl]cycloprop-2-yl}phenoxyphosphate
sodium 2-dimethylamino-5-[1-(3,4,5-trimethoxyphenylcarbonyl]cycloprop-2-yl}phenoxyphosphate
[2-(3-amino-4-methoxyphenyl)cyclopropyl](3,4,5-trimethoxyphenyl)methanone, N-serinamide
[2-(3-amino-4-methylphenyl)cyclopropyl](3,4,5-trimethoxyphenyl)methanone, N-serinamide
[2-(3-amino-4-fluorophenyl)cyclopropyl](3,4,5-trimethoxyphenyl)methanone, N-serinamide
[2-(3-amino-4-dimethylaminophenyl)cyclopropyl](3,4,5-trimethoxyphenyl)methanone, N-serinamide

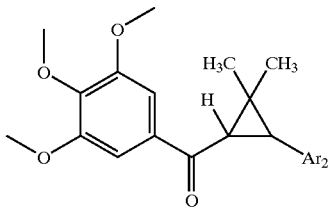

[3,3-dimethyl-2-(3-hydroxy-4-methoxyphenyl)cyclopropyl](3,4,5-trimethoxyphenyl)methanone,
[2-(3-amino-4-methoxyphenyl)-3,3-dimethylcyclopropyl](3,4,5-trimethoxyphenyl)methanone
[3,3-dimethyl-2-(4-dimethylaminophenyl)cyclopropyl](3,4,5-trimethoxyphenyl)methanone
[3,3-dimethyl-2-(4-methoxyphenyl)cyclopropyl](3,4,5-trimethoxyphenyl)methanone
[3,3-dimethyl-2-(4-ethoxyphenyl)cyclopropyl](3,4,5-trimethoxyphenyl)methanone
[3,3-dimethyl-2-(3-hydroxy-4-methylphenyl)cyclopropyl](3,4,5-trimethoxyphenyl)methanone
[2-(3-amino-4-methylphenyl)-3,3-dimethylcyclopropyl](3,4,5-trimethoxyphenyl)methanone
[3,3-dimethyl-2-(3-hydroxy-4-fluorophenyl)cyclopropyl](3,4,5-trimethoxyphenyl)methanone
[2-(3-amino-4-fluorophenyl)-3,3-dimethylcyclopropyl](3,4,5-trimethoxyphenyl)methanone
[3,3-dimethyl-2-(3-hydroxy-4-dimethylaminophenyl)cyclopropyl](3,4,5-trimethoxyphenyl)methanone
[2-(3-amino-4-dimethylaminophenyl)-3,3-dimethylcyclopropyl](3,4,5-trimethoxyphenyl)methanone
{3,3-dimethyl-2-[1-methyl(ethyl)indol-5-yl]cyclopropyl}(3,4,5-trimethoxyphenyl)methanone
{3,3-dimethyl-2-[1-methyl(ethyl)-1,2,3,4-tetrahydroquinol-6-yl]cyclopropyl}(3,4,5-trimethoxyphenyl)methanone
{3,3-dimethyl-2-[1-methyl(ethyl)carbazol-4-yl]cyclopropyl}(3,4,5-trimethoxyphenyl)methanone
2-methoxy-5-[3,3-dimethyl-1-(3,4,5-trimethoxyphenylcarbonyl]cycloprop-2-yl}phenoxyphosphoric acid
2-methyl-5-[3,3-dimethyl-1-(3,4,5-trimethoxyphenylcarbonyl]-2-cycloprop-2-yl}phenoxyphosphoric acid
2-fluoro-5-[3,3-dimethyl-1-(3,4,5-trimethoxyphenylcarbonyl]cycloprop-2-yl}phenoxyphosphoric acid
2-dimethylamino-5-[3,3-dimethyl-1-(3,4,5-trimethoxyphenylcarbonyl]cycloprop-2-yl}phenoxyphosphoric acid
sodium 2-methoxy-5-[3,3-dimethyl-1-(3,4,5-trimethoxyphenylcarbonyl]cycloprop-2-yl}phenoxyphosphate
sodium 2-methyl-5-[3,3-dimethyl-1-(3,4,5-trimethoxyphenylcarbonyl]cycloprop-2-yl}phenoxyphosphate
sodium 2-fluoro-5-[3,3-dimethyl-1-(3,4,5-trimethoxyphenylcarbonyl]cycloprop-2-yl}phenoxyphosphate
sodium 2-dimethylamino-5-[3,3-dimethyl-1-(3,4,5-trimethoxyphenylcarbonyl]cycloprop-2-yl}phenoxyphosphate
[2-(3-amino-4-methoxyphenyl)-3,3-dimethylcyclopropyl](3,4,5-trimethoxyphenyl)methanone, N-serinamide
[2-(3-amino-4-methylphenyl)-3,3-dimethylcyclopropyl](3,4,5-trimethoxyphenyl)methanone, N-serinamide
[2-(3-amino-4-fluorophenyl)-3,3-dimethylcyclopropyl](3,4,5-trimethoxyphenyl)methanone, N-serinamide
[2-(3-amino-4-dimethylaminophenyl)-3,3-dimethylcyclopropyl](3,4,5-trimethoxyphenyl)methanone, N-serinamide

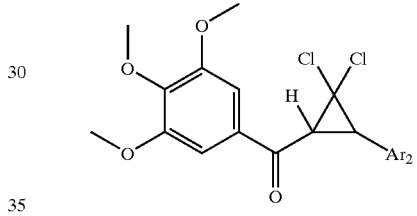

[3,3-dichloro-2-(3-hydroxy-4-methoxyphenyl)cyclopropyl](3,4,5-trimethoxyphenyl)methanone
[2-(3-amino-4-methoxyphenyl)-3,3-dichlorocyclopropyl](3,4,5-trimethoxyphenyl)methanone
[3,3-dichloro-2-(4-dimethylaminophenyl)cyclopropyl](3,4,5-trimethoxyphenyl)methanone
[3,3-dichloro-2-(4-methoxyphenyl)cyclopropyl](3,4,5-trimethoxyphenyl)methanone
[3,3-dichloro-2-(4-ethoxyphenyl)cyclopropyl](3,4,5-trimethoxyphenyl)methanone
[3,3-dichloro-2-(3-hydroxy-4-methylphenyl)cyclopropyl](3,4,5-trimethoxyphenyl)methanone
[2-(3-amino-4-methylphenyl)-3,3-dichlorocyclopropyl](3,4,5-trimethoxyphenyl)methanone
[3,3-dichloro-2-(3-hydroxy-4-fluorophenyl)cyclopropyl](3,4,5-trimethoxyphenyl)methanone
[2-(3-amino-4-fluorophenyl)-3,3-dichlorocyclopropyl](3,4,5-trimethoxyphenyl)methanone
[3,3-dichloro-2-(3-hydroxy-4-dimethylaminophenyl)cyclopropyl](3,4,5-trimethoxyphenyl)methanone
[2-(3-amino-4-dimethylaminophenyl)-3,3-dichlorocyclopropyl](3,4,5-trimethoxyphenyl)methanone
{3,3-dichloro-2-[1-methyl(ethyl)indol-5-yl]cyclopropyl}(3,4,5-trimethoxyphenyl)methanone
{3,3-dichloro-2-[1-methyl(ethyl)-1,2,3,4-tetrahydroquinol-6-yl]cyclopropyl}(3,4,5-trimethoxyphenyl)methanone
{3,3-dichloro-2-[1-methyl(ethyl)carbazol-4-yl]cyclopropyl}(3,4,5-trimethoxyphenyl)methanone
2-methoxy-5-[3,3-dichloro-1-(3,4,5-trimethoxyphenylcarbonyl]cycloprop-2-yl}phenoxyphosphoric acid 2-methyl-5-[3,3-dichloro-1-(3,4,5-trimethoxyphenylcarbonyl]-2-cycloprop-2-yl}phenoxyphosphoric acid
2-fluoro-5-[3,3-dichloro-1-(3,4,5-trimethoxyphenylcarbonyl]cycloprop-2-yl}phenoxyphosphoric acid
2-dimethylamino-5-[3,3-dichloro-1-(3,4,5-trimethoxyphenylcarbonyl]cycloprop-2-yl}phenoxyphosphoric acid
sodium 2-methoxy-5-[3,3-dichloro-1-(3,4,5-trimethoxyphenylcarbonyl]-cycloprop-2-yl}phenoxyphosphate
sodium 2-methyl-5-[3,3-dichloro-1-(3,4,5-trimethoxyphenylcarbonyl]-cycloprop-2-yl}phenoxyphosphate
sodium 2-fluoro-5-[3,3-dichloro-1-(3,4,5-trimethoxyphenylcarbonyl]-cycloprop-2-yl}phenoxyphosphate
sodium 2-dimethylamino-5-[3,3-dichloro-1-(3,4,5-trimethoxyphenylcarbonyl]-cycloprop-2-yl}phenoxyphosphate
[2-(3-amino-4-methoxyphenyl)-3,3-dichlorocyclopropyl](3,4,5-trimethoxyphenyl)methanone, N-serinamide
[2-(3-amino-4-methylphenyl)-3,3-dichlorocyclopropyl](3,4,5-trimethoxyphenyl)methanone, N-serinamide
[2-(3-amino-4-fluorophenyl)-3,3-dichlorocyclopropyl](3,4,5-trimethoxyphenyl)methanone, N-serinamide
[2-(3-amino-4-dimethylaminophenyl)-3,3-dichlorocyclopropyl](3,4,5-trimethoxyphenyl)methanone, N-serinamide

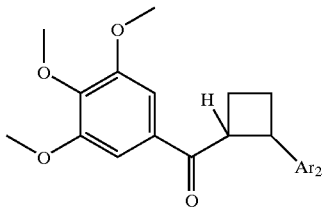

[2-(3-hydroxy-4-methoxyphenyl)cyclobutyl](3,4,5-trimethoxyphenyl)methanone
[2-(3-amino-4-methoxyphenyl)cyclobutyl](3,4,5-trimethoxyphenyl)methanone
[2-(4-dimethylaminophenyl)cyclobutyl](3,4,5-trimethoxyphenyl)methanone
[2-(4-methoxyphenyl)cyclobutyl](3,4,5-trimethoxyphenyl)methanone
[2-(4-ethoxyphenyl)cyclobutyl](3,4,5-trimethoxyphenyl)methanone
[2-(3-hydroxy-4-methylphenyl)cyclobutyl](3,4,5-trimethoxyphenyl)methanone
[2-(3-amino-4-methylphenyl)cyclobutyl](3,4,5-trimethoxyphenyl)methanone
[2-(3-hydroxy-4-fluorophenyl)cyclobutyl](3,4,5-trimethoxyphenyl)methanone
[2-(3-amino-4-fluorophenyl)cyclobutyl](3,4,5-trimethoxyphenyl)methanone
[2-(3-hydroxy-4-dimethylaminophenyl)cyclobutyl](3,4,5-trimethoxyphenyl)methanone
[2-(3-amino-4-dimethylaminophenyl)cyclobutyl](3,4,5-trimethoxyphenyl)methanone
{2-[1-methyl(ethyl)indol-5-yl]cyclobutyl}(3,4,5-trimethoxyphenyl)methanone
{2-[1-methyl(ethyl)-1,2,3,4-tetrahydroquinol-6-yl]cyclobutyl}(3,4,5-trimethoxyphenyl)methanone
{2-[1-methyl(ethyl)carbazol-4-yl]cyclobutyl}(3,4,5-trimethoxyphenyl)methanone
2-methoxy-5-[1-(3,4,5-trimethoxyphenylcarbonyl]cyclobut-2-yl}phenoxyphosphoric acid
2-methyl-5-[1-(3,4,5-trimethoxyphenylcarbonyl]cyclobut-2-yl}phenoxyphosphoric acid
2-fluoro-5-[1-(3,4,5-trimethoxyphenylcarbonyl]cyclobut-2-yl}phenoxyphosphoric acid
2-dimethylamino-5-[1-(3,4,5-trimethoxyphenylcarbonyl]cyclobut-2-yl}phenoxyphosphoric acid
sodium 2-methoxy-5-[1-(3,4,5-trimethoxyphenylcarbonyl]cyclobut-2-yl}phenoxyphosphate
sodium 2-methyl-5-[1-(3,4,5-trimethoxyphenylcarbonyl]cyclobut-2-yl}phenoxyphosphate
sodium 2-fluoro-5-[1-(3,4,5-trimethoxyphenylcarbonyl]cyclobut-2-yl}phenoxyphosphate
sodium 2-dimethylamino-5-[1-(3,4,5-trimethoxyphenylcarbonyl]cyclobut-2-yl}phenoxyphosphate
[2-(3-amino-4-methoxyphenyl)cyclobutyl](3,4,5-trimethoxyphenyl)methanone, N-serinamide
[2-(3-amino-4-methylphenyl)cyclobutyl](3,4,5-trimethoxyphenyl)methanone, N-serinamide
[2-(3-amino-4-fluorophenyl)cyclobutyl](3,4,5-trimethoxyphenyl)methanone, N-serinamide
[2-(3-amino-4-dimethylaminophenyl)cyclobutyl](3,4,5-trimethoxyphenyl)methanone, N-serinamide

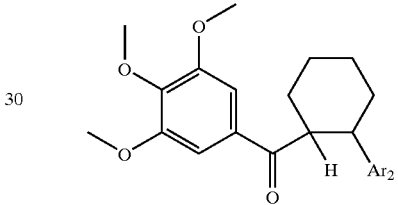

[2-(3-hydroxy-4-methoxyphenyl)cyclohexyl](3,4,5-trimethoxyphenyl)methanone
[2-(3-amino-4-methoxyphenyl)cyclohexyl](3,4,5-trimethoxyphenyl)methanone
[2-(4-dimethylaminophenyl)cyclohexyl](3,4,5-trimethoxyphenyl)methanone
[2-(4-methoxyphenyl)cyclohexyl](3,4,5-trimethoxyphenyl)methanone
[2-(4-ethoxyphenyl)cyclohexyl](3,4,5-trimethoxyphenyl)methanone
[2-(3-hydroxy-4-methylphenyl)cyclohexyl](3,4,5-trimethoxyphenyl)methanone
[2-(3-amino-4-methylphenyl)cyclohexyl](3,4,5-trimethoxyphenyl)methanone
[2-(3-hydroxy-4-fluorophenyl)cyclohexyl](3,4,5-trimethoxyphenyl)methanone
[2-(3-amino-4-fluorophenyl)cyclohexyl](3,4,5-trimethoxyphenyl)methanone
[2-(3-hydroxy-4-dimethylaminophenyl)cyclohexyl](3,4,5-trimethoxyphenyl)methanone
[2-(3-amino-4-dimethylaminophenyl)cyclohexyl](3,4,5-trimethoxyphenyl)methanone
{2-[1-methyl(ethyl)indol-5-yl]cyclohexyl}(3,4,5-trimethoxyphenyl)methanone
{2-[1-methyl(ethyl)-1,2,3,4-tetrahydroquinol-6-yl]cyclohexyl}(3,4,5-trimethoxyphenyl)methanone
{2-[1-methyl(ethyl)carbazol-4-yl]cyclohexyl}(3,4,5-trimethoxyphenyl)methanone
2-methoxy-5-[1-(3,4,5-trimethoxyphenylcarbonyl]cyclohex-2-yl}phenoxyphosphoric acid
2-methyl-5-[1-(3,4,5-trimethoxyphenylcarbonyl]cyclohex-2-yl}phenoxyphosphoric acid 2-fluoro-5-[1-(3,4,5-trimethoxyphenylcarbonyl]cyclohex-2-yl}phenoxyphosphoric acid
2-dimethylamino-5-[1-(3,4,5-trimethoxyphenylcarbonyl]cyclohex-2-yl}phenoxyphosphoric acid
sodium 2-methoxy-5-[1-(3,4,5-trimethoxyphenylcarbonyl][cyclohex-2-yl}phenoxyphosphate
sodium 2-methyl-5-[1-(3,4,5-trimethoxyphenylcarbonyl][cyclohex-2-yl}phenoxyphosphate
sodium 2-fluoro-5-[1-(3,4,5-trimethoxyphenylcarbonyl][cyclohex-2-yl}phenoxyphosphate
sodium 2-dimethylamino-5-[1-(3,4,5-trimethoxyphenylcarbonyl]cyclohex-2-yl}phenoxyphosphate
[2-(3-amino-4-methoxyphenyl)cyclohexyl](3,4,5-trimethoxyphenyl)methanone, N-serinamide
[2-(3-amino-4-methylphenyl)cyclohexyl](3,4,5-trimethoxyphenyl)methanone, N-serinamide
[2-(3-amino-4-fluorophenyl)cyclohexyl](3,4,5-trimethoxyphenyl)methanone, N-serinamide
[2-(3-amino-4-dimethylaminophenyl)cyclohexyl](3,4,5-trimethoxyphenyl)methanone, N-serinamide

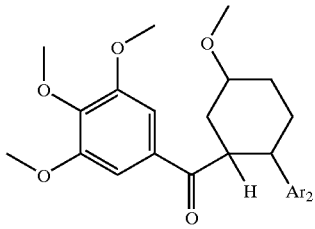

[2-(3-hydroxy-4-methoxyphenyl)-5-methoxycyclohexyl]-(3,4,5-trimethoxyphenyl)methanone
[2-(3-amino-4-methoxyphenyl)-5-methoxycyclohexyl]-(3,4,5-trimethoxyphenyl)methanone
[2-(4-dimethylaminophenyl)-5-methoxycyclohexyl]-(3,4,5-trimethoxyphenyl)methanone
[5-methoxy-2-(4-methoxyphenyl)cyclohexyl]-(3,4,5-trimethoxyphenyl)methanone
[2-(4-ethoxyphenyl)-5-methoxycyclohexyl]-(3,4,5-trimethoxyphenyl)methanone
[2-(3-hydroxy-4-methylphenyl)-5-methoxycyclohexyl]-(3,4,5-trimethoxyphenyl)methanone
[2-(3-amino-4-methylphenyl)-5-methoxycyclohexyl]-(3,4,5-trimethoxyphenyl)methanone
[2-(3-hydroxy-4-fluorophenyl)-5-methoxycyclohexyl]-(3,4,5-trimethoxyphenyl)methanone
[2-(3-amino-4-fluorophenyl)-5-methoxycyclohexyl]-(3,4,5-trimethoxyphenyl)methanone
[2-(3-hydroxy-4-dimethylaminophenyl)-5-methoxycyclohexyl]-(3,4,5-trimethoxyphenyl)methanone
[2-(3-amino-4-dimethylaminophenyl)-5-methoxycyclohexyl]-(3,4,5-trimethoxyphenyl)methanone
{5-methoxy-2-[1-methyl(ethyl)indol-5-yl]cyclohexyl}(3,4,5-trimethoxyphenyl)methanone
{5-methoxy-2-[1-methyl(ethyl)-1,2,3,4-tetrahydroquinol-6-yl]cyclohexyl}(3,4,5-trimethoxyphenyl)methanone
{5-methoxy-2-[1-methyl(ethyl)carbazol-4-yl]cyclohexyl}(3,4,5-trimethoxyphenyl)methanone
2-methoxy-5-[1-(3,4,5-trimethoxyphenylcarbonyl]-5-methoxycyclohex-2-yl}phenoxyphosphoric acid
2-methyl-5-[1-(3,4,5-trimethoxyphenylcarbonyl]-5-methoxycyclohex-2-yl}phenoxyphosphoric acid
2-fluoro-5-[1-(3,4,5-trimethoxyphenylcarbonyl]-5-methoxycyclohex-2-yl}phenoxyphosphoric acid
2-dimethylamino-5-[1-(3,4,5-trimethoxyphenylcarbonyl]-5-methoxycyclohex-2-yl}phenoxyphosphoric acid
sodium 2-methoxy-5-[1-(3,4,5-trimethoxyphenylcarbonyl]-5-methoxycyclohex-2-yl}phenoxyphosphate
sodium 2-methyl-5-[1-(3,4,5-trimethoxyphenylcarbonyl]-5-methoxycyclohex-2-yl}phenoxyphosphate
sodium 2-fluoro-5-[1-(3,4,5-trimethoxyphenylcarbonyl]-5-methoxycyclohex-2-yl}phenoxyphosphate
sodium 2-dimethylamino-5-[1-(3,4,5-trimethoxyphenylcarbonyl]-5-methoxycyclohex-2-yl}phenoxyphosphate
[2-(3-amino-4-methoxyphenyl)-5-methoxycyclohexyl](3,4,5-trimethoxyphenyl)methanone, N-serinamide
[2-(3-amino-4-methylphenyl)-5-methoxycyclohexyl](3,4,5-trimethoxyphenyl)methanone, N-serinamide
[2-(3-amino-4-fluorophenyl)-5-methoxycyclohexyl](3,4,5-trimethoxyphenyl)methanone, N-serinamide
[2-(3-amino-4-dimethylaminophenyl)-5-methoxycyclohexyl](3,4,5-trimethoxyphenyl)methanone, N-serinamide

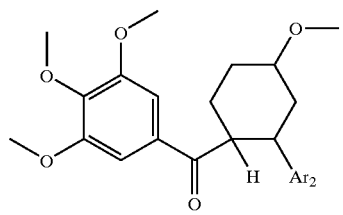

[2-(3-hydroxy-4-methoxyphenyl)-4-methoxycyclohexyl](3,4,5-trimethoxyphenyl)methanone
[2-(3-amino-4-methoxyphenyl)-4-methoxycyclohexyl](3,4,5-trimethoxyphenyl)methanone
[2-(4-dimethylaminophenyl)-4-methoxycyclohexyl](3,4,5-trimethoxyphenyl)methanone
[4-methoxy-2-(4-methoxyphenyl)cyclohexyl](3,4,5-trimethoxyphenyl)methanone
[2-(4-ethoxyphenyl)-4-methoxycyclohexyl](3,4,5-trimethoxyphenyl)methanone
[2-(3-hydroxy-4-methylphenyl)-4-methoxycyclohexyl](3,4,5-trimethoxyphenyl)methanone
[2-(3-amino-4-methylphenyl)-4-methoxycyclohexyl](3,4,5-trimethoxyphenyl)methanone
[2-(3-hydroxy-4-fluorophenyl)-4-methoxycyclohexyl](3,4,5-trimethoxyphenyl)methanone
[2-(3-amino-4-fluorophenyl)-4-methoxycyclohexyl](3,4,5-trimethoxyphenyl)methanone
[2-(3-hydroxy-4-dimethylaminophenyl)-4-methoxycyclohexyl](3,4,5-trimethoxyphenyl)methanone
[2-(3-amino-4-dimethylaminophenyl)-4-methoxycyclohexyl](3,4,5-trimethoxyphenyl)methanone
{4-methoxy-2-[1-methyl(ethyl)indol-5-yl]cyclohexyl}(3,4,5-trimethoxyphenyl)methanone
{4-methoxy-2-[1-methyl(ethyl)-1,2,3,4-tetrahydroquinol-6-yl]cyclohexyl}(3,4,5-trimethoxyphenyl)methanone
{4-methoxy-2-[1-methyl(ethyl)carbazol-4-yl]cyclohexyl}(3,4,5-trimethoxyphenyl)methanone
2-methoxy-5-[1-(3,4,5-trimethoxyphenylcarbonyl]-4-methoxycyclohex-2-yl}phenoxyphosphoric acid
2-methyl-5-[1-(3,4,5-trimethoxyphenylcarbonyl]-4-methoxycyclohex-2-yl}phenoxyphosphoric acid
2-fluoro-5-[1-(3,4,5-trimethoxyphenylcarbonyl]-4-methoxycyclohex-2-yl}phenoxyphosphoric acid
2-dimethylamino-5-[1-(3,4,5-trimethoxyphenylcarbonyl]-4-methoxycyclohex-2-yl}phenoxyphosphoric acid
sodium 2-methoxy-5-[1-(3,4,5-trimethoxyphenylcarbonyl]-4-methoxycyclohex-2-yl}phenoxyphosphate sodium 2-methyl-5-[1-(3,4,5-trimethoxyphenylcarbonyl]-4-methoxycyclohex-2-yl}phenoxyphosphate
sodium 2-fluoro-5-[1-(3,4,5-trimethoxyphenylcarbonyl]-4-methoxycyclohex-2-yl}phenoxyphosphate
sodium 2-dimethylamino-5-[1-(3,4,5-trimethoxyphenylcarbonyl]-4-methoxycyclohex-2-yl}phenoxyphosphate
[2-(3-amino-4-methoxyphenyl)-4-methoxycyclohexyl](3,4,5-trimethoxyphenyl)methanone, N-serinamide
[2-(3-amino-4-methylphenyl)-4-methoxycyclohexyl](3,4,5-trimethoxyphenyl)methanone, N-serinamide
[2-(3-amino-4-fluorophenyl)-4-methoxycyclohexyl](3,4,5-trimethoxyphenyl)methanone, N-serinamide
[2-(3-amino-4-dimethylaminophenyl)-4-methoxycyclohexyl](3,4,5-trimethoxyphenyl)methanone, N-serinamide

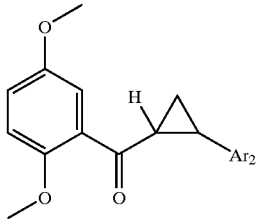

[2-(3-hydroxy-4-methoxyphenyl)cyclopropyl](2,5-dimethoxyphenyl)methanone
[2-(3-amino-4-methoxyphenyl)cyclopropyl](2,5-dimethoxyphenyl)methanone
[2-(4-dimethylaminophenyl)cyclopropyl](2,5-dimethoxyphenyl)methanone
[2-(4-methoxyphenyl)cyclopropyl](2,5-dimethoxyphenyl)methanone
[2-(4-ethoxyphenyl)cyclopropyl](2,5-dimethoxyphenyl)methanone
[2-(3-hydroxy-4-methylphenyl)cyclopropyl](2,5-dimethoxyphenyl)methanone
[2-(3-amino-4-methylphenyl)cyclopropyl](2,5-dimethoxyphenyl)methanone
[2-(3-hydroxy-4-fluorophenyl)cyclopropyl](2,5-dimethoxyphenyl)methanone
[2-(3-amino-4-fluorophenyl)cyclopropyl](2,5-dimethoxyphenyl)methanone
[2-(3-hydroxy-4-dimethylaminophenyl)cyclopropyl](2,5-dimethoxyphenyl)methanone
[2-(3-amino-4-dimethylaminophenyl)cyclopropyl](2,5-dimethoxyphenyl)methanone
{2-[1-methyl(ethyl)indol-5-yl]cyclopropyl}(2,5-dimethoxyphenyl)methanone
{2-[1-methyl(ethyl)-1,2,3,4-tetrahydroquinol-6-yl]cyclopropyl}(2,5-dimethoxyphenyl)methanone
{2-[1-methyl(ethyl)carbazol-4-yl]cyclopropyl}(2,5-dimethoxyphenyl)methanone
2-methoxy-5-[1-(2,5-dimethoxyphenylcarbonyl]cycloprop-2-yl]phenoxyphosphoric acid
2-methyl-5-[1-(2,5-dimethoxyphenylcarbonyl]cycloprop-2-yl]phenoxyphosphoric acid
2-fluoro-5-[1-(2,5-dimethoxyphenylcarbonyl]cycloprop-2-yl]phenoxyphosphoric acid
2-dimethylamino-5-[1-(2,5-dimethoxyphenylcarbonyl]cycloprop-2-yl]phenoxyphosphoric acid
sodium 2-methoxy-5-[1-(2,5-dimethoxyphenylcarbonyl]cycloprop-2-yl}phenoxyphosphate
sodium 2-methyl-5-[1-(2,5-dimethoxyphenylcarbonyl]cycloprop-2-yl}phenoxyphosphate
sodium 2-fluoro-5-[1-(2,5-dimethoxyphenylcarbonyl]cycloprop-2-yl}phenoxyphosphate
sodium 2-dimethylamino-5-[1-(2,5-dimethoxyphenylcarbonyl]cycloprop-2-yl]phenoxyphosphate
[2-(3-amino-4-methoxyphenyl)cyclopropyl](2,5-dimethoxyphenyl)methanone, N-serinamide
[2-(3-amino-4-methylphenyl)cyclopropyl](2,5-dimethoxyphenyl)methanone, N-serinamide
[2-(3-amino-4-fluorophenyl)cyclopropyl](2,5-dimethoxyphenyl)methanone, N-serinamide
[2-(3-amino-4-dimethylaminophenyl)cyclopropyl](2,5-dimethoxyphenyl)methanone, N-serinamide

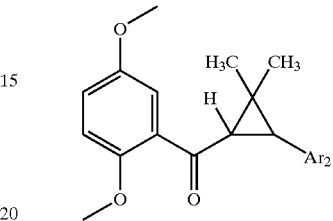

[3,3-dimethyl-2-(3-hydroxy-4-methoxyphenyl)cyclopropyl](2,5-dimethoxyphenyl)methanone
[2-(3-amino-4-methoxyphenyl)-3,3-dimethylcyclopropyl](2,5-dimethoxyphenyl)methanone
[3,3-dimethyl-2-(4-dimethylaminophenyl)cyclopropyl](2,5-dimethoxyphenyl)methanone
[3,3-dimethyl-2-(4-methoxyphenyl)cyclopropyl](2,5-dimethoxyphenyl)methanone
[3,3-dimethyl-2-(4-ethoxyphenyl)cyclopropyl](2,5-dimethoxyphenyl)methanone
[3,3-dimethyl-2-(3-hydroxy-4-methylphenyl)cyclopropyl](2,5-dimethoxyphenyl)methanone
[2-(3-amino-4-methylphenyl)-3,3-dimethylcyclopropyl](2,5-dimethoxyphenyl)methanone
[3,3-dimethyl-2-(3-hydroxy-4-fluorophenyl)cyclopropyl](2,5-dimethoxyphenyl)methanone
[2-(3-amino-4-fluorophenyl)-3,3-dimethylcyclopropyl](2,5-dimethoxyphenyl)methanone
[3,3-dimethyl-2-(3-hydroxy-4-dimethylaminophenyl)cyclopropyl](2,5-dimethoxyphenyl)methanone
[2-(3-amino-4-dimethylaminophenyl)-3,3-dimethylcyclopropyl](2,5-dimethoxyphenyl)methanone
{3,3-dimethyl-2-[1-methyl(ethyl)indol-5-yl]cyclopropyl}(2,5-dimethoxyphenyl)methanone
{3,3-dimethyl-2-[1-methyl(ethyl)-1,2,3,4-tetrahydroquinol-6-yl]cyclopropyl}(2,5-dimethoxyphenyl)methanone
{3,3-dimethyl-2-[1-methyl(ethyl)carbazol-4-yl]cyclopropyl}(2,5-dimethoxyphenyl)methanone
2-methoxy-5-[3,3-dimethyl-1-(2,5-dimethoxyphenylcarbonyl]cycloprop-2-yl}phenoxyphosphoric acid
2-methyl-5-[3,3-dimethyl-1-(2,5-dimethoxyphenylcarbonyl]-2-cycloprop-2-yl}phenoxyphosphoric acid
2-fluoro-5-[3,3-dimethyl-1-(2,5-dimethoxyphenylcarbonyl]cycloprop-2-yl}phenoxyphosphoric acid
2-dimethylamino-5-[3,3-dimethyl-1-(2,5-dimethoxyphenylcarbonyl]cycloprop-2-yl}phenoxyphosphoric acid
sodium 2-methoxy-5-[3,3-dimethyl-1-(2,5-dimethoxyphenylcarbonyl]cycloprop-2-yl}phenoxyphosphate
sodium 2-methyl-5-[3,3-dimethyl-1-(2,5-dimethoxyphenylcarbonyl]cycloprop-2-yl}phenoxyphosphate
sodium 2-fluoro-5-[3,3-dimethyl-1-(2,5-dimethoxyphenylcarbonyl]cycloprop-2-yl}phenoxyphosphate sodium 2-dimethylamino-5-[3,3-dimethyl-1-(2,5-dimethoxyphenylcarbonyl]cycloprop-2-yl}phenoxyphosphate
[2-(3-amino-4-methoxyphenyl)-3,3-dimethylcyclopropyl]-(2,5-dimethoxyphenyl)methanone, N-serinamide
[2-(3-amino-4-methylphenyl)-3,3-dimethylcyclopropyl]-(2,5-dimethoxyphenyl)methanone, N-serinamide
[2-(3-amino-4-fluorophenyl)-3,3-dimethylcyclopropyl](2,5-dimethoxyphenyl)methanone, N-serinamide
[2-(3-amino-4-dimethylaminophenyl)-3,3-dimethylcyclopropyl](2,5-dimethoxyphenyl)methanone, N-serinamide

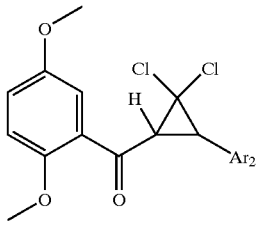

[3,3-dichloro-2-(3-hydroxy-4-methoxyphenyl)cyclopropyl](2,5-dimethoxyphenyl)methanone
[2-(3-amino-4-methoxyphenyl)-3,3-dichlorocyclopropyl](2,5-dimethoxyphenyl)methanone
[3,3-dichloro-2-(4-dimethylaminophenyl)cyclopropyl](2,5-dimethoxyphenyl)methanone
[3,3-dichloro-2-(4-methoxyphenyl)cyclopropyl](2,5-dimethoxyphenyl)methanone
[3,3-dichloro-2-(4-ethoxyphenyl)cyclopropyl](2,5-dimethoxyphenyl)methanone
[3,3-dichloro-2-(3-hydroxy-4-methylphenyl)cyclopropyl](2,5-dimethoxyphenyl)methanone
[2-(3-amino-4-methylphenyl)-3,3-dichlorocyclopropyl](2,5-dimethoxyphenyl)methanone
[3,3-dichloro-2-(3-hydroxy-4-fluorophenyl)cyclopropyl](2,5-dimethoxyphenyl)methanone
[2-(3-amino-4-fluorophenyl)-3,3-dichlorocyclopropyl](2,5-dimethoxyphenyl)methanone
[3,3-dichloro-2-(3-hydroxy-4-dimethylaminophenyl)cyclopropyl](2,5-dimethoxyphenyl)methanone
[2-(3-amino-4-dimethylaminophenyl)-3,3-dichlorocyclopropyl](2,5-dimethoxyphenyl)methanone
{3,3-dichloro-2-[1-methyl(ethyl)indol-5-yl]cyclopropyl}(2,5-dimethoxyphenyl)methanone
{3,3-dichloro-2-[1-methyl(ethyl)-1,2,3,4-tetrahydroquinol-6-yl]cyclopropyl}(2,5-dimethoxyphenyl)methanone
{3,3-dichloro-2-[1-methyl(ethyl)carbazol-4-yl]cyclopropyl}(2,5-dimethoxyphenyl)methanone
2-methoxy-5-[3,3-dichloro-1-(2,5-dimethoxyphenylcarbonyl]cycloprop-2-yl}phenoxyphosphoric acid
2-methyl-5-[3,3-dichloro-1-(2,5-dimethoxyphenylcarbonyl]-2-cycloprop-2-yl}phenoxyphosphoric acid
2-fluoro-5-[3,3-dichloro-1-(2,5-dimethoxyphenylcarbonyl]cycloprop-2-yl}phenoxyphosphoric acid
2-dimethylamino-5-[3,3-dichloro-1-(2,5-dimethoxyphenylcarbonyl]cycloprop-2-yl}phenoxyphosphoric acid
sodium 2-methoxy-5-[3,3-dichloro-1-(2,5-dimethoxyphenylcarbonyl]cycloprop-2-yl}phenoxyphosphate
sodium 2-methyl-5-[3,3-dichloro-1-(2,5-dimethoxyphenylcarbonyl]cycloprop-2-yl}phenoxyphosphate
sodium 2-fluoro-5-[3,3-dichloro-1-(2,5-dimethoxyphenylcarbonyl]cycloprop-2-yl}phenoxyphosphate
sodium 2-dimethylamino-5-[3,3-dichloro-1-(2,5-dimethoxyphenylcarbonyl]cycloprop-2-yl}phenoxyphosphate
[2-(3-amino-4-methoxyphenyl)-3,3-dichlorocyclopropyl](2,5-dimethoxyphenyl)methanone, N-serinamide
[2-(3-amino-4-methylphenyl)-3,3-dichlorocyclopropyl](2,5-dimethoxyphenyl)methanone, N-serinamide
[2-(3-amino-4-fluorophenyl)-3,3-dichlorocyclopropyl](2,5-dimethoxyphenyl)methanone, N-serinamide
[2-(3-amino-4-dimethylaminophenyl)-3,3-dichlorocyclopropyl](2,5-dimethoxyphenyl)methanone, N-serinamide

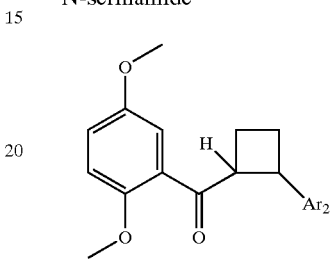

[2-(3-hydroxy-4-methoxyphenyl)cyclobutyl](2,5-dimethoxyphenyl)methanone
[2-(3-amino-4-methoxyphenyl)cyclobutyl](2,5-dimethoxyphenyl)methanone
[2-(4-dimethylaminophenyl)cyclobutyl](2,5-dimethoxyphenyl)methanone
[2-(4-methoxyphenyl)cyclobutyl](2,5-dimethoxyphenyl)methanone
[2-(4-ethoxyphenyl)cyclobutyl](2,5-dimethoxyphenyl)methanone
[2-(3-hydroxy-4-methylphenyl)cyclobutyl](2,5-dimethoxyphenyl)methanone
[2-(3-amino-4-methylphenyl)cyclobutyl](2,5-dimethoxyphenyl)methanone
[2-(3-hydroxy-4-fluorophenyl)cyclobutyl](2,5-dimethoxyphenyl)methanone
[2-(3-amino-4-fluorophenyl)cyclobutyl](2,5-dimethoxyphenyl)methanone
[2-(3-hydroxy-4-dimethylaminophenyl)cyclobutyl](2,5-dimethoxyphenyl)methanone
[2-(3-amino-4-dimethylaminophenyl)cyclobutyl](2,5-dimethoxyphenyl)methanone
{2-[1-methyl(ethyl)indol-5-yl]cyclobutyl}(2,5-dimethoxyphenyl)methanone
{2-[1-methyl(ethyl)-1,2,3,4-tetrahydroquinol-6-yl]cyclobutyl}(2,5-dimethoxyphenyl)methanone
{2-[1-methyl(ethyl)carbazol-4-yl]cyclobutyl}(2,5-dimethoxyphenyl)methanone
2-methoxy-5-[1-(2,5-dimethoxyphenylcarbonyl]cyclobut-2-yl}phenoxyphosphoric acid
2-methyl-5-[1-(2,5-dimethoxyphenylcarbonyl]cyclobut-2-yl}phenoxyphosphoric acid
2-fluoro-5-[1-(2,5-dimethoxyphenylcarbonyl]cyclobut-2-yl}phenoxyphosphoric acid
2-dimethylamino-5-[1-(2,5-dimethoxyphenylcarbonyl]cyclobut-2-yl}phenoxyphosphoric acid
sodium 2-methoxy-5-[1-(2,5-dimethoxyphenylcarbonyl]cyclobut-2-yl}phenoxyphosphate
sodium 2-methyl-5-[1-(2,5-dimethoxyphenylcarbonyl]cyclobut-2-yl}phenoxyphosphate
sodium 2-fluoro-5-[1-(2,5-dimethoxyphenylcarbonyl]cyclobut-2-yl}phenoxyphosphate sodium 2-dimethylamino-5-[1-(2,5-dimethoxyphenylcarbonyl]cyclobut-2-yl}phenoxyphosphate
[2-(3-amino-4-methoxyphenyl)cyclobutyl](2,5-dimethoxyphenyl)methanone, N-serinamide
[2-(3-amino-4-methylphenyl)cyclobutyl](2,5-dimethoxyphenyl)methanone, N-serinamide
[2-(3-amino-4-fluorophenyl)cyclobutyl](2,5-dimethoxyphenyl)methanone, N-serinamide
[2-(3-amino-4-dimethylaminophenyl)cyclobutyl](2,5-dimethoxyphenyl)methanone, N-serinamide

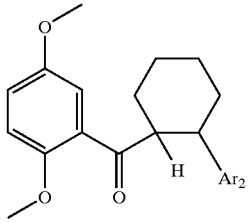

[2-(3-hydroxy-4-methoxyphenyl)cyclohexyl](2,5-dimethoxyphenyl)methanone
[2-(3-amino-4-methoxyphenyl)cyclohexyl](2,5-dimethoxyphenyl)methanone
[2-(4-dimethylaminophenyl)cyclohexyl](2,5-dimethoxyphenyl)methanone
[2-(4-methoxyphenyl)cyclohexyl](2,5-dimethoxyphenyl)methanone
[2-(4-ethoxyphenyl)cyclohexyl](2,5-dimethoxyphenyl)methanone
[2-(3-hydroxy-4-methylphenyl)cyclohexyl](2,5-dimethoxyphenyl)methanone
[2-(3-amino-4-methylphenyl)cyclohexyl](2,5-dimethoxyphenyl)methanone
[2-(3-hydroxy-4-fluorophenyl)cyclohexyl](2,5-dimethoxyphenyl)methanone
[2-(3-amino-4-fluorophenyl)cyclohexyl](2,5-dimethoxyphenyl)methanone
[2-(3-hydroxy-4-dimethylaminophenyl)cyclohexyl](2,5-dimethoxyphenyl)methanone
[2-(3-amino-4-dimethylaminophenyl)cyclohexyl](2,5-dimethoxyphenyl)methanone
{2-[1-methyl(ethyl)indol-5-yl]cyclohexyl}(2,5-dimethoxyphenyl)methanone
{2-[1-methyl(ethyl)-1,2,3,4-tetrahydroquinol-6-yl]cyclohexyl}(2,5-dimethoxyphenyl)methanone
{2-[1-methyl(ethyl)carbazol-4-yl]cyclohexyl}(2,5-dimethoxyphenyl)methanone
2-methoxy-5-[1-(2,5-dimethoxyphenylcarbonyl]cyclohex-2-yl}phenoxyphosphoric acid
2-methyl-5-[1-(2,5-dimethoxyphenylcarbonyl]cyclohex-2-yl}phenoxyphosphoric acid
2-fluoro-5-[1-(2,5-dimethoxyphenylcarbonyl]cyclohex-2-yl}phenoxyphosphoric acid
2-dimethylamino-5-[1-(2,5-dimethoxyphenylcarbonyl]cyclohex-2-yl}phenoxyphosphoric acid
sodium 2-methoxy-5-[1-(2,5-dimethoxyphenylcarbonyl]cyclohex-2-yl}phenoxyphosphate
sodium 2-methyl-5-[1-(2,5-dimethoxyphenylcarbonyl]cyclohex-2-yl}phenoxyphosphate
sodium 2-fluoro-5-[1-(2,5-dimethoxyphenylcarbonyl]cyclohex-2-yl}phenoxyphosphate
sodium 2-dimethylamino-5-[1-(2,5-dimethoxyphenylcarbonyl]cyclohex-2-yl}phenoxyphosphate
[2-(3-amino-4-methoxyphenyl)cyclohexyl](2,5-dimethoxyphenyl)methanone, N-serinamide
[2-(3-amino-4-methylphenyl)cyclohexyl](2,5-dimethoxyphenyl)methanone, N-serinamide
[2-(3-amino-4-fluorophenyl)cyclohexyl](2,5-dimethoxyphenyl)methanone, N-serinamide
[2-(3-amino-4-dimethylaminophenyl)cyclohexyl](2,5-dimethoxyphenyl)methanone, N-serinamide

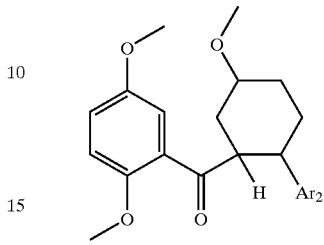

[2-(3-hydroxy-4-methoxyphenyl)-5-methoxycyclohexyl](2,5-dimethoxyphenyl)methanone
[2-(3-amino-4-methoxyphenyl)-5-methoxycyclohexyl](2,5-dimethoxyphenyl)methanone
[2-(4-dimethylaminophenyl)-5-methoxycyclohexyl](2,5-dimethoxyphenyl)methanone
[5-methoxy-2-(4-methoxyphenyl)cyclohexyl](2,5-dimethoxyphenyl)methanone
[2-(4-ethoxyphenyl)-5-methoxycyclohexyl](2,5-dimethoxyphenyl)methanone
[2-(3-hydroxy-4-methylphenyl)-5-methoxycyclohexyl](2,5-dimethoxyphenyl)methanone
[2-(3-amino-4-methylphenyl)-5-methoxycyclohexyl](2,5-dimethoxyphenyl)methanone
[2-(3-hydroxy-4-fluorophenyl)-5-methoxycyclohexyl](2,5-dimethoxyphenyl)methanone
[2-(3-amino-4-fluorophenyl)-5-methoxycyclohexyl](2,5-dimethoxyphenyl)methanone
[2-(3-hydroxy-4-dimethylaminophenyl)-5-methoxycyclohexyl](2,5-dimethoxyphenyl)methanone
[2-(3-amino-4-dimethylaminophenyl)-5-methoxycyclohexyl](2,5-dimethoxyphenyl)methanone
{5-methoxy-2-[1-methyl(ethyl)indol-5-yl]cyclohexyl}(2,5-dimethoxyphenyl)methanone
{5-methoxy-2-[1-methyl(ethyl)-1,2,3,4-tetrahydroquinol-6-yl]cyclohexyl}(2,5-dimethoxyphenyl)methanone
{5-methoxy-2-[1-methyl(ethyl)carbazol-4-yl]cyclohexyl}(2,5-dimethoxyphenyl)methanone
2-methoxy-5-[1-(2,5-dimethoxyphenylcarbonyl]-5-methoxycyclohex-2-yl}phenoxyphosphoric acid
2-methyl-5-[1-(2,5-dimethoxyphenylcarbonyl]-5-methoxycyclohex-2-yl}phenoxyphosphoric acid
2-fluoro-5-[1-(2,5-dimethoxyphenylcarbonyl]-5-methoxycyclohex-2-yl}phenoxyphosphoric acid
2-dimethylamino-5-[1-(2,5-dimethoxyphenylcarbonyl]-5-methoxycyclohex-2-yl}phenoxyphosphoric acid
sodium 2-methoxy-5-[1-(2,5-dimethoxyphenylcarbonyl]-5-methoxycyclohex-2-yl]phenoxyphosphate
sodium 2-methyl-5-[1-(2,5-dimethoxyphenylcarbonyl]-5-methoxycyclohex-2-yl]phenoxyphosphate
sodium 2-fluoro-5-[1-(2,5-dimethoxyphenylcarbonyl]-5-methoxycyclohex-2-yl]phenoxyphosphate
sodium 2-dimethylamino-5-[1-(2,5-dimethoxyphenylcarbonyl]-5-methoxycyclohex-2-yl]phenoxyphosphate
[2-(3-amino-4-methoxyphenyl)-5-methoxycyclohexyl]-(2,5-dimethoxyphenyl)methanone, N-serinamide
[2-(3-amino-4-methylphenyl)-5-methoxycyclohexyl]-(2,5-dimethoxyphenyl)methanone, N-serinamide
[2-(3-amino-4-fluorophenyl)-5-methoxycyclohexyl]-(2,5-dimethoxyphenyl)methanone, N-serinamide

[2-(3-amino-4-dimethylaminophenyl)-5-methoxycyclohexyl]-(2,5-dimethoxyphenyl)methanone, N-serinamide

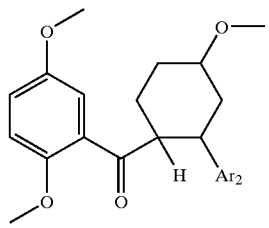

[2-(3-hydroxy-4-methoxyphenyl)-4-methoxycyclohexyl](2,5-dimethoxyphenyl)methanone
[2-(3-amino-4-methoxyphenyl)-4-methoxycyclohexyl](2,5-dimethoxyphenyl)methanone
[2-(4-dimethylaminophenyl)-4-methoxycyclohexyl](2,5-dimethoxyphenyl)methanone
[4-methoxy-2-(4-methoxyphenyl)cyclohexyl](2,5-dimethoxyphenyl)methanone
[2-(4-ethoxyphenyl)-4-methoxycyclohexyl](2,5-dimethoxyphenyl)methanone
[2-(3-hydroxy-4-methylphenyl)-4-methoxycyclohexyl](2,5-dimethoxyphenyl)methanone
[2-(3-amino-4-methylphenyl)-4-methoxycyclohexyl](2,5-dimethoxyphenyl)methanone
[2-(3-hydroxy-4-fluorophenyl)-4-methoxycyclohexyl](2,5-dimethoxyphenyl)methanone
2-(3-amino-4-fluorophenyl)-4-methoxycyclohexyl](2,5-dimethoxyphenyl)methanone
[2-(3-hydroxy-4-dimethylaminophenyl)-4-methoxycyclohexyl](2,5-dimethoxyphenyl)methanone
[2-(3-amino-4-dimethylaminophenyl)-4-methoxycyclohexyl](2,5-dimethoxyphenyl)methanone
{4-methoxy-2-[1-methyl(ethyl)indol-5-yl]cyclohexyl}(2,5-dimethoxyphenyl)methanone
{4-methoxy-2-[1-methyl(ethyl)-1,2,3,4-tetrahydroquinol-6-yl]cyclohexyl}(2,5-dimethoxyphenyl)methanone
{4-methoxy-2-[1-methyl(ethyl)carbazol-4-yl]cyclohexyl}(2,5-dimethoxyphenyl)methanone
2-methoxy-5-[1-(2,5-dimethoxyphenylcarbonyl]-4-methoxycyclohex-2-yl}phenoxyphosphoric acid
2-methyl-5-[1-(2,5-dimethoxyphenylcarbonyl]-4-methoxycyclohex-2-yl}phenoxyphosphoric acid
2-fluoro-5-[1-(2,5-dimethoxyphenylcarbonyl]-4-methoxycyclohex-2-yl}phenoxyphosphoric acid
2-dimethylamino-5-[1-(2,5-dimethoxyphenylcarbonyl]-4-methoxycyclohex-2-yl}phenoxyphosphoric acid
sodium 2-methoxy-5-[1-(2,5-dimethoxyphenylcarbonyl]-4-methoxycyclohex-2-yl}phenoxyphosphate
sodium 2-methyl-5-[1-(2,5-dimethoxyphenylcarbonyl]-4-methoxycyclohex-2-yl}phenoxyphosphate
sodium 2-fluoro-5-[1-(2,5-dimethoxyphenylcarbonyl]-4-methoxycyclohex-2-yl}phenoxyphosphate
sodium 2-dimethylamino-5-[1-(2,5-dimethoxyphenylcarbonyl]-4-methoxycyclohex-2-yl}phenoxyphosphate
[2-(3-amino-4-methoxyphenyl)-4-methoxycyclohexyl](2,5-dimethoxyphenyl)methanone, N-serinamide
[2-(3-amino-4-methylphenyl)-4-methoxycyclohexyl](2,5-dimethoxyphenyl)methanone, N-serinamide
[2-(3-amino-4-fluorophenyl)-4-methoxycyclohexyl](2,5-dimethoxy-dimethoxyphenyl)methanone, N-serinamide
[2-(3-amino-4-dimethylaminophenyl)-4-methoxycyclohexyl](2,5-dimethoxyphenyl)methanone, N-serinamide A product in accordance with the invention may be used as agent for inhibiting tubulin polymerization.

A product in accordance with the invention may be used to promote the disintegration of lumps of cells originating from a vascular tissue.

A product in accordance with the invention may be used for the manufacture of a medicinal product that is useful for treating a pathological condition, such as a cancer.

The present invention also relates to therapeutic compositions containing a compound according to the invention, in combination with an excipient that is pharmaceutically acceptable according to the chosen mode of administration. The pharmaceutical composition may be in solid or liquid form or in the form of liposomes.

Among the solid compositions that may be mentioned are powders, gel capsules and tablets. Among the oral forms that may also be included are solid forms protected against the acidic medium of the stomach. The supports used for the solid forms may be mineral supports, for instance phosphates or carbonates, or organic supports, for instance lactose, celluloses, starch or polymers. The liquid forms may be solutions, suspensions or dispersions. They may contain as dispersive support either water or an organic solvent (ethanol, NMP or the like) or mixtures of surfactants and solvents or complexing agents and solvents.

The liquid forms may be injectable and, as a result, will have a formulation that is acceptable for such a use.

Administration routes by injection that are acceptable include the intravenous, intraperitoneal, intramuscular and subcutaneous routes.

The administered dose of the compounds of the invention may be adapted by the doctor as a function of the route of administration for the patient and the patient's condition.

The compounds of the present invention may be administered alone or as a mixture with other anticancer agents. Among the possible combinations that may be mentioned are:

alkylating agents such as cyclophosphamide, melphalan, ifosfamide, chlorambucil, bulsulfan, thiotepa, prednimustine, carmustine, lomustine, semustine, streptozotocin, decarbazine, temozolomide, procarbazine and hexamethylmelamine platinum derivatives such as cisplatin, carboplatin or oxaliplatin antibiotic agents such as bleomycin, mitomycin or dactinomycin antimicrotubule agents such as vinblastine, vincristine, vindesin, vinorelbin and taxoids (paclitaxel and docetaxel)

anthracyclines such as doxorubicin, daunorubicin, idarubicin, epirubicin, mitoxantrone and losoxantrone group I and II topoisomerases such as etoposide, teniposide, amsacrine, irinotecan, topotecan and tomudex fluoropyrimidines such as 5-fluorouracil, UFT and floxuridine cytidine analogs such as 5-azacytidine, cytarabine, gemcitabine, 6-mercaptomurine and 6-thioguanine adenosine analogs such as pentostatin, cytarabine or fludarabine phosphate methotrexate and folinic acid various enzymes and compounds such as L-asparaginase, hydroxyurea, trans-retinoic acid, suramine, dexrazoxane, amifostine, herceptin and also estrogenic and androgenic hormones antivascular agents such as combretastatine derivatives or colchicine derivatives and prodrugs thereof.

It is also possible to combine the compounds of the present invention with a radiotherapy. These treatments may be administered simultaneously, separately or sequentially. The treatment will be adapted by the doctor as a function of the patient to be treated.

A product in accordance with the invention may promote the disintegration of lumps of cells originating from a vascular tissue. For instance, the products of the present invention may be used in their first therapeutic application to inhibit the growth of cancer cells and at the same time the destruction of existing vessels. The inhibition of vascularization is determined by a cell detachment test as described below.

Test for Determining the Inhibition of Vascularization

A test to determine the detachment of endothelial cells was established in order to select the products on the basis of their "in vitro" activity. This test for determining the endothelial cell detachment is characterized in that the endothelial cells, inoculated in plates which are coated at the bottom with a binder, e.g., chosen from gelatin, fibronectin or vitronectin, after culturing, are supplemented with a medium containing the test compound, and the cells are then labeled with a fluorescent substance, the cells which become detached are removed by washing and the fluorescence of the remaining cells is counted in a fluorimeter.

This test consists in measuring the detachment of endothelial cells cultured on substrates based on a binder, e.g., chosen from fibronectin, vitronectin and gelatin. One day after inoculating the cells in plates containing 96 wells, for example, the culture medium is replaced with a medium containing the test compound in the absence of serum. The same preparation is prepared six times at three different concentrations (0.1, 0.3 and 0.6 $\mu$M) and the control without addition of antivascular product is prepared six times. After treatment for two hours with the test substance, the cells are labeled with calcein-AM (1.6 $\mu$g/ml) in a culture medium supplemented with 0.1% BSA. The cells which become detached are removed by washing with the culture medium containing 0.1% bovine serum albumin; 100 $\mu$l of medium are added to each well. The fluorescence of the remaining cells is counted in a fluorimeter. The data obtained are expressed relative to the control (untreated cells).

The assessment of the detachment of the endothelial cells in vitro is determined in the following way. HDMEC cells (Human Dermal Microvascular Endothelial Cells, Promocell, c-122102) are cultured in an ECGM-MV medium containing 5% fetal calf serum, growth factors (EGF 10 ng/ml, hydrocortisone 1 $\mu$g/ml, 0.4% growth supplement with heparin) and antibiotics (amphotericine 50 ng/ml, gentamicin 50 $\mu$/ml). For the detachment test, the HDMECs are inoculated at a rate of 5 000 cells in clear-bottomed 96-well plates (Costar) precoated with fibronectin (10 $\mu$g/ml) or vitronectin (1 $\mu$g/ml) or gelatin. Twenty-four hours later, the culture medium is replaced with 0.1% BSA ECGM-MV medium containing the indicated products. The test concentrations are 0.1–0.3 and 1 $\mu$M for each product. After treatment for two hours, the cells are labeled for 1 hour with calcein (1.6 $\mu$g/ml, Molecular Probes) in 0.1% BSA ECGM-MV medium. The detached cells are then removed by washing with 0.1% BSA ECGM-MV medium; 100 $\mu$l of medium are added to each well. The fluorescence of the cells which remain attached to the substratum of the well is counted using a fluorimeter, Spectrafluor Plus (Tecan, excitation at 485 nm, and emission at 535 nm). The data are the average of six different samples and are expressed as a percentage of the control (untreated cells).

A cell detachment effect of greater than or equal to 15% is considered as significant.

A product in accordance with the invention may be useful for inhibiting tubulin polymerization in vitro.

Assessment of the Inhibition of Tubulin Polymerization

Tubulin is purified from pig brains according to the published methods (Shelanski et al., 1973, Proc. Natl, Acad. Sci. USA, 70, 765–768. Weingarten et al., 1975, Proc. Natl, Acad. Sci. USA, 72, 1858–1862). Briefly, the brains are ground and centrifuged in an extraction buffer. The tubulin, contained in the extract supernatant, is subjected to two successive cycles of polymerization at 37° C. and depolymerization at 4° C., before being separated from the MAPs (Microtubule Associated Proteins) by chromatography on a phosphocellulose P11 column (Whatman). The tubulin thus isolated is more than 95% pure. It is stored in a buffer known as RB/2 30% glycerol, the composition of which is MES-NaOH [2-(N-morpholino)ethanesulfonic acid] 50 mM, pH 6.8; $MgCl_2$ 0.25 mM; EGTA 0.5 mM; 30% glycerol (v/v), GTP (guanosine 5'-triphosphate) 0.2 mM.

The polymerization of the tubulin into microtubules is monitored by turbidimetry as follows; the tubulin is adjusted to a concentration of 10 $\mu$M (1 mg/ml) in the RB/2 30% glycerol buffer, to which is added 1 mM GTP and 6 mM $MgCl_2$. The polymerization is initiated by increasing the temperature from 6° C. to 37° C. in a cuvette with a 1 cm optical pathlength, placed in a Uvikon 931 spectrophotometer (Kontron) equipped with a thermostatically-regulated cuvette holder. The increase in the turbidity of the solution is monitored at 350 nm.

The products are dissolved at 10 mM in DMSO and added at variable concentrations (0.5 to 10 $\mu$M) to the tubulin solution before polymerization. The $IC_{50}$ value is defined as the concentration of product which inhibits 50% of the rate of polymerization. A product whose $IC_{50}$ value is less than or equal to 3 $\mu$M is considered as very active.

Assessment of the Inhibition of Proliferation of HeLa Cells

The proliferation of HeLa cells is assessed by measuring the incorporation of [$^{14}$C]-thymidine in the following way. The HeLa cells (epithelial tumor cells of human origin) are cultured in a DMEM medium (Gibco) which contains 10% fetal calf serum and antibiotics (1% penicillin, 1% streptomycin). To carry out the proliferation test, the cells are inoculated into 96-well cytostar microplates (Amersham), at a rate of 5 000 cells per well. [$^{14}$C]-thymidine (0.1 $\mu$Ci/well) and the products to be assessed are then added. Variable concentrations of product up to 10 $\mu$M are used; the DMSO (solvent used to dissolve the products) should not exceed 0.5% in the medium. After incubation for 48 hours at 37° C., the radioactivity incorporated into the cells is measured by counting the plate in a TRI-LUX counter (Wallac). The $IC_{50}$ value is defined as the concentration of product which reduces the radioactivity by 50% relative to an untreated control. A product whose $IC_{50}$ value is less than 1 $\mu$M is considered as cytotoxic.

Assessment of the Detachment Effect on HDMEC Endothelial Cells

The assessment of the detachment of the endothelial cells in vitro is determined in the following way. HDMEC cells (Human Dermal Microvascular Endothelial Cells, Promocell, c-122102) are cultured in an ECGM-MV medium containing 5% fetal calf serum, growth factors (EGF 10 ng/ml, hydrocortisone 1 $\mu$/ml, 0.4% growth supplement with heparin) and antibiotics (amphotericine 50 ng/ml, gentamicin 50 $\mu$g/ml). For the detachment test, the HDMECs are inoculated at a rate of 5 000 cells in clear-bottomed 96-well plates (Costar) precoated with fibronectin (10 µg/ml) or vitronectin (1 µg/ml) or gelatin. Twenty-four hours later, the culture medium is replaced with 0.1% BSA ECGM-MV medium containing the indicated products. The test concentrations are 0.1–0.3 and 1 µM for each product. After treatment for two hours, the cells are labeled for 1 hour with calcein (1.6 µg/ml, Molecular Probes) in 0.1% BSA ECGM-MV medium. The detached cells are then removed by washing with 0.1% BSA ECGM-MV medium; 100 µl of medium are added to each well. The fluorescence of the cells which remain attached to the substratum of the well is counted using a fluorimeter, Spectrafluor Plus (Tecan, excitation at 485 nm, and emission at 535 nm). The data are the average of six different samples and are expressed as a percentage of the control (untreated cells).

A cell detachment effect of greater than or equal to 15% is considered as significant.

Definitions

"Halogen" is an element chosen from F, Cl, Br and I.

"Cycloalkyl" may be a substituent chosen from cyclopropyl, cyclobutyl, cyclopentyl, cyclohexyl, cycloheptyl, bicyclo[2.2.1]heptyl and bicyclo[2.2.2]octyl.

"Cycloalkylalkyl" is an alkyl substituent, itself substituted with a cycloalkyl group, for example as defined above.

A substituent defined by "nitrogenous heterocycle containing from 5 to 12 carbon atoms" may be chosen from the group consisting of: 3-pyridyl, 4-pyridyl, 4-pyrimidinyl, 6-quinolyl, 7-quinolyl, 6-isoquinolyl, 7-isoquinolyl, 6-quinazolinyl, 6-quinoxalinyl, N-alkyl-5-indolyl, N-alkyl-6-indolyl, N-alkyl-1,2,3,4-tetrahydro-6-quinolyl, N-alkyl-1,2,3,4-tetrahydro-7-quinolyl, 2-acridinyl, 3-acridinyl, N-alkyl-2-carbazolyl or N-alkyl-3-carbazolyl.

"Aryl" is a substituent comprising at least one aromatic ring, said ring optionally comprising one or more hetero atoms participating in the aromaticity. An example of an aryl group may be a substituent chosen from phenyl, naphthyl, indenyl, pyridyl, pyrimidinyl, pyrazinyl, thienyl, furyl, pyrolyl, thiazolyl, oxazolyl, thiadiazolyl, oxadiazolyl, imidazolyl, quinoleyl, isoquinoleyl, benzothienyl, benzofuryl, indolyl, benzothiazolyl, benzoxazolyl, benzimidazolyl, indazolyl and azaindolyl.

"Heteroaryl" is an aryl group comprising at least one hetero atom participating in the aromaticity. Consequently, aryl groups such as phenyl, naphthyl, anthracenyl and pyrenyl, which do not contain endocyclic hetero atoms, do not form part of the group of heteroaryls.

"Aralkyl" is an alkyl substituent, itself substituted with an aryl group as defined above. A benzyl group is an example of an aralkyl substituent.

The term "substituted" that is especially present in the expressions "substituted alkyl" and "substituted aralkyl" necessarily relates to a substituent other than H, which may be chosen from alkyl, F, Cl, Br, I, N(R7, R8), N(O)(R7, R8), NO, NO$_2$, O(R7), S(R7), SO(R7), SO$_2$(R7), OSO$_2$(R7), PO$_3$(R7), OPO$_3$(R7), CO(R7), COO—(R7), CONH—(R7), CON(R7, R8), CN, C≡C—(R7), N═C—(R9), aryl, aralkyl; in which R7, R8 are independently selected from the group consisting of H, alkyl, alkylene, aryl, aralkyl, C(O)—(R7), C(S)—(R7), alkyl-O(R7), alkyl-S(R7) and alkyl-N (R7, R8), in which, when R7 and R8 are simultaneously present, they may be linked together to form a ring, R9 is selected from the group consisting of alkyl, alkylene, aryl, aralkyl, alkyl-O(R7), alkyl-S(R7) and alkyl-N(R7, R8); and to any other acceptable substituents known to those skilled at the art.

"Amino acid" comprises the natural and artificial amino acids, in enantiomerically pure form or as a mixture.

"5- to 12-membered nitrogenous heterocycle" may be a heterocycle selected from the group consisting of: 3-pyridyl, 4-pyridyl, 4-pyrimidinyl, 6-quinolyl, 7-quinolyl, 6-isoquinolyl, 7-isoquinolyl, 6-quinazolinyl, 6-quinoxalinyl, N-alkyl-5-indolyl, N-alkyl-6-indolyl, N-alkyl-1,2,3,4-tetrahydro-6-quinolyl, N-alkyl-1,2,3,4-tetrahydro-7-quinolyl, 2-acridinyl, 3-acridinyl, N-alkyl-2-carbazolyl or N-alkyl-3-carbazolyl.

The products of general formula (I)

(I)

in which:

A represents a saturated or partially unsaturated monocycloalkyl or bicycloalkyl radical containing from 3 to 14 carbon atoms, optionally substituted with one or more groups chosen from halogen atoms and alkyl, amino, alkylamino, dialkylamino, hydroxyl, alkoxy, alkylthio, carbonyl, cyano, trifluoromethyl, carboxyl, alkoxycarbonyl, carboxamido, N-alkylcarboxamido or N,N-dialkylcarboxamido radicals, X represents an oxygen atom, a radical N—OR' in which R' represents an alkyl or arylalkyl radical optionally substituted with an amino radical, alkylamino, dialkylamino, hydroxyl, alkoxy, alkylthio, carboxyl, alkoxycarbonyl, carboxamido, N-alkylcarboxamido or N,N-dialkylcarboxamido;

R represents a hydrogen or halogen atom, an alkyl or arylalkyl radical optionally substituted with an amino radical, alkylamino, dialkylamino, hydroxyl, alkoxy, alkylthio, carboxyl, alkoxycarbonyl, carboxamido, N-alkylcarboxamido or N,N-dialkylcarboxamido;

Ar$_1$ represents a phenyl nucleus substituted with 1 to 4 methoxy radicals, or a methylenedioxy radical, or an ethylenedioxy radical, or 1 or 2 methoxy radicals and a methylenedioxy radical, or 1 or 2 methoxy radicals and an ethylenedioxy radical;

Ar$_2$ represents:
a phenyl nucleus substituted with one or more groups chosen from halogen atoms and hydroxyl, alkyl, alkoxy, alkylthio, amino, alkylamino and dialkylamino radicals, it being understood that the hydroxyl or amino radicals may be in the form of a cleavable, more water-soluble prodrug such as, in a nonlimiting manner, a phosphate or an amino acid derivative, or
a 5- to 12-membered nitrogenous heterocycle containing 1 or 2 nitrogen atoms, e.g., chosen from 3-pyridyl, 4-pyridyl, 4-pyrimidinyl, 6-quinolyl, 7-quinolyl, 6-isoquinolyl, 7-isoquinolyl, 6-quinazolinyl, 6-quinoxalinyl, N-alkyl-5-indolyl, N-alkyl-6-indolyl, N-alkyl-1,2,3,4-tetrahydro-6-quinolyl, N-alkyl-1,2,3,4-tetrahydro-7-quinolyl, 2-acridinyl, 3-acridinyl, N-alkyl-2-carbazolyl and N-alkyl-3-carbazolyl, it being understood that the relative stereochemistry of the groups C(O)Ar$_1$ and Ar$_2$ on the cycloalkyl A may be trans;

may be obtained by a cycloaddition reaction, of 2+1 or 2+2 or 2+3 or 2+4 type, starting with a chalcone of general formula (II), in which R, Ar$_1$ and Ar$_2$ are defined as above and X represents an oxygen atom, according to the general scheme (I) below, to give the products of general formula (I) in which X represents an oxygen atom, optionally followed by the action of a hydroxylamine $H_2N$—$OR'$ to give the products of general formula (I) in which X represents a radical N—$OR'$.

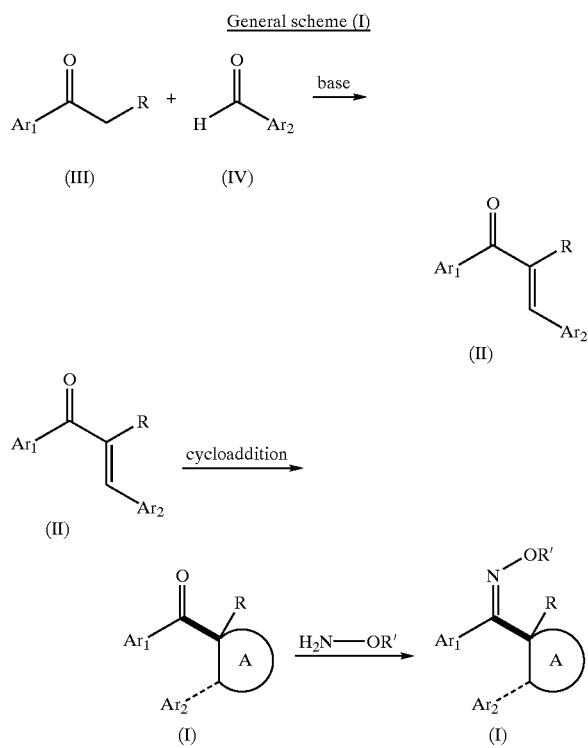

It is possible to use the cycloaddition methods, of 2+1 or 2+2 or 2+3 or 2+4 type, that are known to those skilled in the art such as those described in:

Advances in cycloaddition Vol. I (1988) (editor D. Curran),
Advances in cycloaddition Vol. II (1990) (editor D. Curran),
Advances in cycloaddition Vol. III (1993) (editor D. Curran),
Advances in cycloaddition Vol. IV (1997) (editor M. Lauters),
Advances in cycloaddition Vol. I (1999) (editor M. Harmaka),
1,3-Dipolar cycloaddition Vol. I and Vol. II (1984) (editor A. Padwa).

When $Ar_2$ represents a phenyl nucleus substituted with a hydroxyl or amino radical, this function may be protected prior to the cycloaddition reaction, and then deprotected under the conditions described in Protective Groups in Organic Chemistry, 1981 (T. Greene, editor Wiley). When said substituent is a hydroxyl radical, a silyl group such as the tert-butyldimethylsilyl (TBDMS) group may be used, and when said substituent represents an amino radical, a nitro radical or an alkyloxycarbonyl group such as tert-butyloxycarbonyl (Boc) or benzyloxycarbonyl (Cbz) may be used.

When A represents a cyclopropyl radical, the chalcone of general formula (II) may be reacted with a reagent such as, in a nonlimiting manner, a sulfoxonium or sulfonium ylide or a phosphonium ylide or a diazomethane derivative or a malonic derivative of a carbene generated in situ.

When A represents a cyclobutyl radical, the chalcone of general formula (II) may be reacted with an electron-rich ethylenic derivative such as, in a nonlimiting manner, a 1,1-dialkylethylene or 1,1-dialkoxyethylene or a trialkylsilyloxyethylene or a 3-trialkylstannylpropene.

When A represents a cyclopentyl radical, the chalcone of general formula (II) may be reacted with a "trimethylenemethane equivalent" derivative, in the presence of a palladium catalyst such as, in a nonlimiting manner, that described in J. Amer. Chem. Soc. (1983), 105, 2315.

When A represents a cyclopentyl radical, the chalcone of general formula (II) may be reacted with a butadiene derivative.

When A represents a bicyclo[2.2.1]heptyl or bicyclo[2.2.2]octyl radical, the chalcone of general formula (II) may be reacted with a cyclopentadiene or 1,3-cyclohexadiene derivative, respectively.

It is understood that the cycloaddition reactions on a chalcone may be performed enantioselectively or enantiospecifically using either a chiral reagent or a chiral catalyst.

It is also understood that, since the cycloaddition produces a product containing unsaturation, said unsaturation may be reduced by one of the conventional methods widely described, for example a catalytic hydrogenation using a transition metal, especially palladium, optionally in the presence of an activity-moderating poison to enable a selective hydrogenation, on an acceptable support, for example activated charcoal, alumina or asbestos.

The chalcones of general formula (I) are generally prepared by coupling, in the presence of a base and of a dehydrating agent, between an aromatic ketone of general formula (III) and an aromatic aldehyde of general formula (IV), according, for example and in a nonlimiting manner, to J. Med. Chem., 1990, 33, 1948.

The aromatic ketones of general formula (III) and the aldehydes of general formula (IV) are either commercially available or are described in the literature, or are prepared by standard methods for synthesizing aromatic ketones or aldehydes that are known to those skilled in the art.

According to a second general synthetic scheme, the products of general formula (I) may be prepared from 2-arylcycloalkanecarboxylate derivatives of general formula (V) in which A, R and $Ar_2$ are defined as above. Two different routes are thus possible:

either acylation, of Friedel-Crafts type, of a product of general formula $Ar_1H$ with a derivative of general formula (V) in which X represents a halogen atom, such as a chlorine atom, or a hydroxyl radical, in the presence of an acid catalyst that is either mineral, for instance polyphosphoric acid or trifluoroacetic acid or trifluoromethanesulfonic acid, or a Lewis acid such as aluminum trichloride, tin tetrachloride, titanium tetrachloride or boron trifluoride complexed with diethyl ether. This method is advantageous since the portion $Ar_1$ of the products of general formula (I) corresponds to aromatic nuclei that are electron-rich and thus highly reactive in acylation reactions of Friedel-Crafts type;

or the reaction of an organometallic reagent, such as an organomagnesium or an organolithium reagent, with a derivative of general formula (V), in which X will represent a halogen atom, such as a chlorine atom, or a hydroxyl radical, or a radical $NR_1R_2$, in which $R_1$ and $R_2$ may be other than a hydrogen atom and in which $R_1$ may represent a methyl radical and $R_2$ may represent a methoxy radical, to form a derivative known as a "Weinreb amide".

$Ar_1/H$ Friedel-Crafts

General scheme (II)

$$\begin{array}{c} X\text{-CO-R(A)-Ar}_2 \\ (V) \end{array} \xrightarrow[\substack{X = Cl, OH \\ Ar_1M \\ X = Cl, OH, NR_1R_2, OR_1 \\ M = MgBr(Cl), Li\ldots}]{} \begin{array}{c} Ar_1\text{-CO-R(A)-Ar}_2 \\ (I) \end{array} \xrightarrow{H_2N-OR'} \begin{array}{c} Ar_1\text{-C(=NOR')-R(A)-Ar}_2 \\ (I) \end{array}$$

The products of general formula (V) are either known or are prepared according to the known methods for synthesizing 2-arylcycloalkanecarboxylates.

By way of nonlimiting example:
the 2-arylcyclopropanecarboxylates may be prepared by a cycloaddition of 2+1 type or a cinnamate derivative, using the methods described in general scheme (I), or by electrochemical coupling of a cinnamate derivative with dibromomethane, according to J. Org. Chem., 1990, 55, 2503, or by reacting a stilbene derivative with ethyl diazoacetate according to J. Chem. Soc., Chem. Commun., 1985, 328;

the 2-arylcyclobutanecarboxylates may be prepared by a cycloaddition of 2+2 type of a cinnamate derivative, using the methods described in general scheme (I), or by electrochemical coupling of a cinnamate derivative with a 1,2-dibromoethane, according to J. Org. Chem., 1990, 55, 2503, or by decarboxylation of a 2-arylcyclobutane-1,1-dicarboxylate according to J. Het. Chem., 1995, 1493;

the 2-arylcyclopropanecarboxylates may be prepared by a cycloaddition of 2+1 type of a cinnamate derivative, using the methods described in the general scheme (I) or by electrochemical coupling of a cinnamate derivative with a 1,3-dibromopropane, according to J. Org. Chem., 1990, 55, 2503, or by enantioselective arylation of a cyclopent-1-enecaboxylate with an aryllithium reagent, according to J. Org. Chem., 1992, 57, 4300;

the 2-arylcyclohexanecarboxylates may be prepared by a cycloaddition of 2+1 type of a cinnamate derivative, using the methods described in the general scheme (I), or by electrochemical coupling of a cinnamate derivative with a 1,4-dibromobutane, according to J. Org. Chem., 1990, 55, 2503, or by enantioselective arylation of a cyclohex-1-enecarboxylate with an aryllithium reagent, according to J. Org. Chem., 1992, 57, 4300, or by a cycloaddition of Diels-Alder type between a 4-arylbutadiene and an acrylate, according to U.S. Pat. No. 5,866,513.

The aromatic compounds of general formula $Ar_1H$ are either commercially available or are prepared according to the methods described in the literature, and the organometallic compounds of general formula $Ar_1M$ are either commercially available or are prepared from corresponding halo derivatives, such as bromo or chloro derivatives, which are themselves commercially available or prepared according to the methods described in the literature.

EXAMPLE 1

[2-(3-Hydroxy-4-methoxyphenyl)cyclopropyl](3,4,5-trimethoxyphenyl)methanone, trans racemate Step 1: 5 g of E-3-(3-hydroxy-4-methoxyphenyl)-1-(3,4,5-trimethoxyphenyl)propenone, which may be obtained according to Bioorg. Med. Chem. Lett (1998), 8, 1051, were dissolved in 75 mL of DMF in a 250 mL three-necked flask. 2.4 g of tert-butyldimethyldichlorosilane and 1.08 g of imidazole were then added. After stirring for 20 hours at room temperature, the reaction medium was poured into 400 mL of water. The mixture was extracted 3 times with 75 mL of ethyl acetate and the combined organic phases were then washed with water, dried over magnesium sulfate and concentrated under reduced pressure. 6.6 g of E-3-(3-tert-butyldimethylsilyloxy-4-methoxyphenyl)-1-(3,4,5-trimethoxyphenyl)propenone were thus obtained, and were used without further purification in the following step.

Step 2: 124 mg of sodium hydride, as a 60% suspension in oil, and 10 mL of DMSO were added to a 50 mL three-necked flask under an argon atmosphere. 660 mg of trimethylsulfoxonium iodide were then added portionwise and the mixture was stirred for 1 hour after the evolution of gas had ceased. 1.38 g of E-3-(3-tert-butyldimethylsilyloxy-4-methoxyphenyl)-1-(3,4,5-trimethoxyphenyl)propenone were then added portionwise over 15 minutes, and the mixture was stirred for 20 hours at room temperature. The reaction medium was then poured onto 200 mL of water and 100 g of crushed ice, and then extracted 3 times with 75 mL of ethyl acetate. The combined organic phases were washed with water and dried over magnesium sulfate. After concentrating under reduced pressure, the oily orange residue obtained was purified by flash chromatography on silica gel (70–230 mesh), eluting with a mixture of cyclohexane and ethyl acetate (70/30 by volume). 0.9 g of a yellow gum was thus obtained, which was recrystallized from 5 mL of diisopropyl ether, to give 650 mg of pure [2-(3-hydroxy-4-methoxyphenyl)-cyclopropyl](3,4,5-trimethoxyphenyl)methanone, trans racemate, the characteristics of which were as follows:

melting point (Kofler)=75° C.

elemental analysis: % C=66.43%; % H=6.15%.

EXAMPLE 2

[2-(4-Dimethylaminophenyl)cyclopropyl](3,4,5-trimethoxyphenyl)methanone, trans racemate Working as in step 2 of example 1, but starting with 1 g of E-3-(4-dimethylaminophenyl)-1-(3,4,5-trimethoxyphenyl)propenone, which may be obtained according to J. Med. Chem. (1990), 33, 1948, and after purification by flash chromatography on silica gel (70–230 mesh) eluting with a mixture of cyclohexane and ethyl acetate (70/30 by volume), 650 mg of pure [2-(4-dimethylaminophenyl)cyclopropyl](3,4,5-trimethoxyphenyl)methanone, trans racemate, were obtained in the form of an oil, the characteristic of which was as follows:

$^1$H NMR spectrum (300 MHz, (CD$_3$)$_2$SO, δ in ppm): 1.51 (mt: 1H); 1.64 (mt: 1H); 2.47 (mt: 1H); 2.88 (s: 6H); 3.11 (mt: 1H); 3.76 (s: 3H); 3.86 (s: 6H); 6.69 (broad d, J=9 Hz: 2H); 7.11 (broad d, J=9 Hz: 2H); 7.34 (s: 2H).

EXAMPLE 3

[2-(3-Hydroxy-4-methoxyphenyl)bicyclo[2.2.1]hept-4-enyl](3,4,5-trimethoxyphenyl)methanone, trans racemate Step 1: 566 mg of freshly distilled cyclopentadiene and 1 mL of dichloromethane were added to a 25 mL three-necked flask under an argon atmosphere, the system was then cooled to 0° C. and 1.07 g of tin tetrachloride, in pentahydrate form, were added. 1.38 g of E-3-(3-tert-butyldimethylsilyloxy-4-methoxyphenyl)-1-(3,4,5-trimethoxyphenyl)propenone, prepared in step 1 of example 1, dissolved in 4 mL of dichloromethane were then added dropwise at 0° C. After stirring for 4 hours at 0° C., the mixture was allowed to warm to room temperature and was stirred for a further 16 hours at room temperature. After addition of 10 mL of water and 5 mL of dichloromethane, the pH was adjusted to 8 by addition of saturated sodium bicarbonate solution. The organic phase was separated out and the aqueous phase was then re-extracted twice with 10 mL of dichloromethane. The combined organic phases were washed with water, dried over sodium sulfate and concentrated under reduced pressure. The crude product was purified by flash chromatography on silica gel (70–230 mesh), eluting with a mixture of cyclohexane and ethyl acetate (80/20 by volume). 700 mg of [2-(3-tert-butyldimethylsilyloxy-4-methoxyphenyl)bicyclo[2.2.1]hept-4-enyl](3,4,5-trimethoxyphenyl)methanone, trans racemate containing about 10% cis racemate, were thus obtained in the form of a yellow oil which was used without further purification in the following step.

Step 2: A solution of 700 mg of [2-(3-tert-butyldimethylsilyloxy-4-methoxyphenyl)bicyclo[2.2.1]hept-4-enyl[(3,4,5-trimethoxyphenyl)methanone in 10 mL of THF in a 25 mL three-necked flask was cooled to 0° C. 1.49 mL of a 1M solution of tetrabutylammonium fluoride in THF were then added. After stirring for one hour at 0° C., the mixture was allowed to warm to room temperature and was stirred for a further 5 hours at room temperature. The reaction medium was then poured into 50 mL of water and extracted 3 times with 20 mL of ethyl acetate. The combined organic phases were washed with water, dried over magnesium sulfate and concentrated under reduced pressure. The crude product was purified by flash chromatography on silica gel (70–230 mesh), eluting with a mixture of cyclohexane and ethyl acetate (70/30 by volume). 270 mg of [2-(3-hydroxy-4-methoxyphenyl)bicyclo[2.2.1]hept-4-enyl](3,4,5-trimethoxyphenyl)methanone, trans racemate containing about 5% cis racemate, were thus obtained in the form of a cream-colored powder, the characteristics of which were as follows:

melting point (Kofler)=152° C.
elemental analysis: % C=70.38, % H=6.09.

BIOLOGICAL RESULTS

| Example No. | Tubulin: inhibition of polymerization IC$_{50}$ (µM) | HeLa cells: inhibition of proliferation IC$_{50}$ (µM) | HDMEC cells: inhibition of proliferation IC$_{50}$ (µM) | Percentage of detachment of HDMEC cells induced with the compound cited in the example at a concentration of 1 µM |
|---|---|---|---|---|
| 1 | 1.0 | <0.0019 | 0.017–0.018 | 36–37 |
| 2 | 2.5 | 1.35/1.45 | 4 | nd |
| 3 | 4.5 | 0.52–1.06 | nd | nd | nd: not determined

What is claimed is:

1. A product corresponding to formula (I) below:

in which:

A represents a saturated or partially unsaturated, optionally substituted cyclic hydrocarbon containing from 3 to 14 carbon atoms;

X is selected from O and N—O—(R2), each radical R or (R2) is independently selected from H, C1–C7 alkyl, cyclo(C3–C9)alkyl(C1–C7)alkylaryl (C1–C7)alkyl-, substituted C1–C7 alkyl, substituted cyclo(C3–C9)alkyl(C1–C7)alkyl-, and substituted aryl (C1–C7)alkyl-, or R is a halogen and (R2) is as defined above, Ar$_1$ represents a first phenyl nucleus, substituted with 1 to 4 radicals O(R3), in which R3 is independently selected from H and C1–C3 alkyl, and in which an R3 may be simultaneously linked to two adjacent oxygen atoms borne by the, first phenyl nucleus, and Ar$_2$ is selected from 3-hydroxy-4-methoxyphenyl; 4-hydroxy-3-methoxyphenyl; 3-hydroxy-4-aminophenyl; 4-hydroxy-3-aminophenyl; 3-hydroxy-4-(N,N-dimethylamino)phenyl; and 4-hydroxy-3-(N,N-dimethylamino)phenyl.

2. The product as claimed in claim 1, wherein A is a monocyclic or bicyclic hydrocarbon containing from 3 to 8 carbon atoms.

3. The product as claimed in claim 2, wherein A is a cyclopropyl.

4. The product as claimed in any one of claims 1 to 3, wherein X is oxygen.

5. The product as claimed in any one of claims 1 to 3, wherein R is selected from H, halogen, CH$_3$, CF$_3$, C$_2$H$_5$, and C$_3$–C$_4$ alkyl.

6. The product as claimed in any one of claims 1 to 3, wherein the first phenyl nucleus Ar$_1$ is substituted with a substituent or a group of substituents chosen from:

(i) 1 to 4 OCH$_3$ radicals, (ii) a methylenedioxy radical, (iii) an ethylenedioxy radical, (iv) 1 or 2 OCH$_3$ radicals and a methylenedioxy radical, and (v) 1 or 2 OCH$_3$ radicals and an ethylenedioxy radical.

7. The product as claimed in claim 6, wherein Ar$_1$ is substituted with a group of substituents chosen from:

(i) 2,5-dimethoxy, (ii) 3,5-dimethoxy, (iii) 2,3,4-trimethoxy, (iv) 3,4,5-trimethoxy, (v) 2,4,5-trimethoxy, (vi) 2,3,5-trimethoxy, (vii) 2,3,4,5-tetramethoxy, (viii) 3,4-methylenedioxy, and (ix) 3,4-ethylenedioxy.

8. The product as claimed in any one of claims 1 to 3, wherein the product is:

1) in racemic form, 2) in a form enriched in one stereoisomer, or 3) in a form enriched inane enantiomer, and wherein the product is optionally salified.

9. A pharmaceutical composition comprising a product as claimed in any one of claims 1 to 3, in combination with a pharmaceutically acceptable excipient.

10. A method for inhibiting in-vitro tubulin polymerization, comprising administering to a host in need of such treatment a pharmaceutically effective amount of the product of any one of claims 1 to 3.

11. A method for promoting the disintegration of lumps in HeLa and HDMEC cells, comprising administering to a host in need of such treatment a pharmaceutically effective amount of the product of any one of claims 1 to 3.

12. A method for treating a pathological condition associated with HDMEC cells, comprising administering to a host in need of such treatment a pharmaceutically effective amount of the product of any one of claims 1 to 3.

13. The method as claimed in claim 12, wherein the pathological condition is cancer.

* * * * *